United States Patent
Elbe et al.

(10) Patent No.: US 7,176,228 B2
(45) Date of Patent: Feb. 13, 2007

(54) PYRAZOLE BIPHENYLCARBOXAMIDES

(75) Inventors: Hans-Ludwig Elbe, Wuppertal (DE); Heiko Rieck, Foy-lès-Lyon (FR); Ralf Dunkel, Monheim (DE); Ulrike Wachendorff-Neumann, Neuwied (DE); Astrid Mauler-Machnik, Leichlingen (DE); Karl-Heinz Kuck, Langenfeld (DE); Martin Kugler, Leichlingen (DE); Thomas Jaetsch, Köln (DE)

(73) Assignee: Bayer Cropscience AG, Monheim (DE)

( * ) Notice: Subject to any disclaimer, the term of this patent is extended or adjusted under 35 U.S.C. 154(b) by 464 days.

(21) Appl. No.: 10/333,598

(22) PCT Filed: Jul. 11, 2001

(86) PCT No.: PCT/EP01/07981

§ 371 (c)(1),
(2), (4) Date: May 6, 2003

(87) PCT Pub. No.: WO02/08197

PCT Pub. Date: Jan. 31, 2002

(65) Prior Publication Data

US 2004/0039043 A1 Feb. 26, 2004

(30) Foreign Application Priority Data

Jul. 24, 2000 (DE) ................. 100 35 857
May 9, 2001 (DE) ................. 101 22 447

(51) Int. Cl.
*A61K 31/415* (2006.01)
*C07D 231/10* (2006.01)
*C07D 231/12* (2006.01)
*C07D 231/16* (2006.01)

(52) U.S. Cl. .................... 514/406; 548/374.1
(58) Field of Classification Search ............... 514/406; 548/374.1
See application file for complete search history.

(56) References Cited

U.S. PATENT DOCUMENTS

| 5,045,554 A | 9/1991 | Alt et al. ................. 514/365 |
| 5,223,526 A | 6/1993 | McLoughlin ............... 514/406 |
| 5,330,995 A | 7/1994 | Eicken et al. .............. 514/355 |
| 5,416,103 A | 5/1995 | Eicken et al. .............. 514/355 |
| 5,438,070 A | 8/1995 | Eicken et al. .............. 514/403 |
| 5,480,897 A | 1/1996 | Eicken et al. .............. 514/365 |
| 5,556,988 A | 9/1996 | Eicken et al. ........... 548/374.1 |
| 5,589,493 A | 12/1996 | Eicken et al. .............. 514/355 |
| 6,147,214 A | 11/2000 | Ragan ....................... 546/143 |
| 6,271,237 B1* | 8/2001 | Galemmo et al. .......... 514/256 |
| 6,369,069 B1 | 4/2002 | Kleemann et al. .......... 514/277 |
| 6,369,093 B1* | 4/2002 | Elbe et al. ................. 514/406 |
| 6,992,098 B2* | 1/2006 | Elbe et al. ................. 514/406 |
| 2004/0053971 A1* | 3/2004 | Elbe et al. ................. 514/341 |
| 2005/0182120 A1* | 8/2005 | Elbe et al. ................. 514/406 |
| 2005/0186120 A1* | 8/2005 | Dorian et al. ............... 422/101 |
| 2006/0116414 A1* | 6/2006 | Dunkel et al. .............. 514/406 |

FOREIGN PATENT DOCUMENTS

| WO | 91/01311 | 2/1991 |
| WO | 99/09013 | 2/1999 |
| WO | 00/09482 | 2/2000 |
| WO | 00/14071 | 3/2000 |
| WO | WO 200014071 A2 * | 3/2000 |

OTHER PUBLICATIONS

Synth. Commun., 30, (month unavailable) 2000, pp. 665-669, Pravin M. Bendale & Bhushan M. Khadilkar, "Silica Gel Supported Chromium Trioxide: An Efficient Reagent for Oxidative Cleavage or Oximes to Carbonyl Compounds Under Mild Condidtion".

Synth. Commun. 29, (month unavailable) 1999, pp. 1697-1701, Hajipour A.R., Mohammadpoor-Baltork, I, Nikbaghat, K, and Imanzadeh, G., "Solid-Phase Synthesis of Oximes".

Tetrahedron Letters, vol. 28, No. 43, (month unavailable) 1987, pp. 5093-5096, M.J. Sharp et al, "Synthetic Connections to the Aromatic Directed Metalation Reaction. Functionalized Aryl Boronic Acids by IPSO Borodesilyation. General Syntheses of Unsymmetrical Biphenyls and m-Terphenyls".

* cited by examiner

*Primary Examiner*—Kamal A. Saeed
*Assistant Examiner*—Nyeemah Grazier
(74) *Attorney, Agent, or Firm*—Richard E. L. Henderson

(57) ABSTRACT

The invention relates to biphenylcarboxamides of the formula (I)

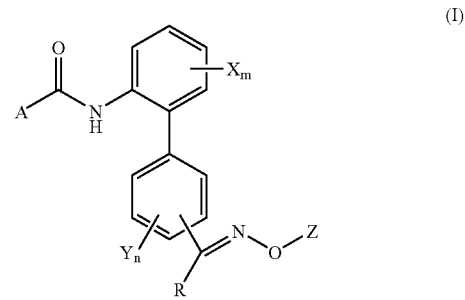

in which A, R, Z, X, Y, m and n are each as defined in the disclosure, to a plurality of processes for preparing these substances, to their use for controlling undesirable microorganisms, and to novel intermediates and their preparation.

6 Claims, No Drawings

PYRAZOLE BIPHENYLCARBOXAMIDES

The present invention relates to novel biphenylcarboxamides, to a plurality of processes for their preparation and to their use for controlling undesirable micro-organisms.

It is already known that numerous carboxanilides have fungicidal properties (cf. WO 93/11 117, WO 99/09 013, WO 00/14 071, EP-A 0 545 099 and EP-A 0 589 301). The activity of these substances is good; however, in some cases, it is unsatisfactory.

Novel biphenylcarboxamides of the formula (I)

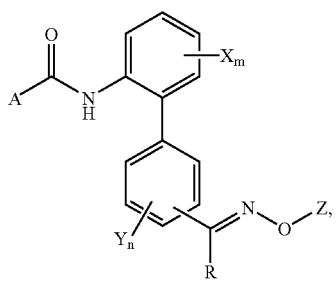

in which
R represents hydrogen, $C_1$–$C_6$-alkyl, $C_3$–$C_6$-cycloalkyl or represents $C_1$–$C_6$-halogenoalkyl having 1 to 5 halogen atoms,
Z represents hydrogen, $C_1$–$C_6$-alkyl or represents $C_1$–$C_6$-halogenoalkyl having 1 to 5 halogen atoms,
X and Y independently of one another each represent halogen, nitro, cyano, hydroxy, carboxyl, $C_1$–$C_8$-alkyl, $C_1$–$C_6$-halogenoalkyl having 1 to 5 halogen atoms, $C_1$–$C_8$-alkoxy, $C_1$–$C_6$-halogenoalkoxy having 1 to 5 halogen atoms, $C_1$–$C_8$-alkylthio, $C_1$–$C_6$-halogenoalkylthio having 1 to 5 halogen atoms, $C_2$–$C_8$-alkenyloxy, $C_2$–$C_8$-halogenoalkenyloxy having 1 to 5 halogen atoms, $C_3$–$C_8$-alkinyloxy, $C_3$–$C_8$-halogenoalkinyloxy having 1 to 5 halogen atoms, $C_3$–$C_8$-cycloalkyl, $C_1$–$C_8$-alkoxycarbonyl, $C_1$–$C_8$-alkylsulphinyl, $C_1$–$C_8$-alkylsulphonyl, $C_1$–$C_8$-halogenoalkylsulphinyl having 1 to 5 halogen atoms, $C_1$–$C_8$-halogenoalkylsulphonyl having 1 to 5 halogen atoms or $C_1$–$C_6$-alkoximino-$C_1$–$C_6$-alkyl,
m represents integers from 0 to 3, where X represents identical or different radicals if m represents 2 or 3,
n represents integers from 0 to 4, where Y represents identical or different radicals, if n represents 2, 3 or 4, and
A represents a radical of the formula

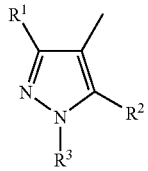

in which
α) $R^1$ represents hydrogen, cyano, halogen, nitro, $C_1$–$C_4$-alkyl, $C_1$–$C_4$-halogenoalkyl having 1 to 5 halogen atoms, $C_3$–$C_6$-cycloalkyl, $C_1$–$C_4$-alkoxy, $C_1$–$C_4$-halogenoalkoxy having 1 to 5 halogen atoms, $C_1$–$C_4$-alkylthio, $C_1$–$C_4$-halogenoalkylthio having 1 to 5 halogen atoms, aminocarbonyl, or aminocarbonyl-$C_1$–$C_4$-alkyl and $R^2$ represents hydrogen, chlorine, bromine, iodine, cyano, $C_1$–$C_4$-alkyl, $C_1$–$C_4$-alkoxy or $C_1$–$C_4$-alkylthio and
$R^3$ represents hydrogen, $C_1$–$C_4$-alkyl, $C_1$–$C_4$-halogenoalkyl having 1 to 5 halogen atoms, hydroxy-$C_1$–$C_4$-alkyl, $C_2$–$C_6$-alkenyl, $C_3$–$C_6$-cycloalkyl, $C_1$–$C_4$-alkylthio-$C_1$–$C_4$-alkyl, $C_1$–$C_4$-halogenoalkylthio-$C_1$–$C_4$-alkyl having 1 to 5 halogen atoms, $C_1$–$C_4$-alkoxy-$C_1$–$C_4$-alkyl, $C_1$–$C_4$-halogenoalkoxy-$C_1$–$C_4$-alkyl having 1 to 5 halogen atoms or phenyl, or β) $R^1$ represents hydrogen, cyano, halogen, nitro, $C_2$–$C_4$-alkyl, $C_1$–$C_4$-halogenoalkyl having 1 to 5 halogen atoms, $C_3$–$C_6$-cycloalkyl, $C_1$–$C_4$-alkoxy, $C_1$–$C_4$-halogenoalkoxy having 1 to 5 halogen atoms, $C_1$–$C_4$-alkylthio, $C_1$–$C_4$-halogenoalkylthio having 1 to 5 halogen atoms, aminocarbonyl, or aminocarbonyl-$C_1$–$C_4$-alkyl and
$R^2$ represents fluorine and
$R^3$ represents hydrogen, $C_1$–$C_4$-alkyl, $C_1$–$C_4$-halogenoalkyl having 1 to 5 halogen atoms, hydroxy-$C_1$–$C_4$-alkyl, $C_2$–$C_6$-alkenyl, $C_3$–$C_6$-cycloalkyl, $C_1$–$C_4$-alkylthio-$C_1$–$C_4$-alkyl, $C_1$–$C_4$-halogenoalkylthio-$C_1$–$C_4$-alkyl having 1 to 5 halogen atoms, $C_1$–$C_4$-alkoxy-$C_1$–$C_4$-alkyl, $C_1$–$C_4$-halogenoalkoxy-$C_1$–$C_4$-alkyl having 1 to 5 halogen atoms or phenyl, or γ) $R^1$ represents hydrogen, cyano, halogen, nitro, $C_1$–$C_4$-alkyl, $C_1$–$C_4$-halogenoalkyl having 1 to 5 halogen atoms, $C_3$–$C_6$-cycloalkyl, $C_1$–$C_4$-alkoxy, $C_1$–$C_4$-halogenoalkoxy having 1 to 5 halogen atoms, $C_1$–$C_4$-alkylthio, $C_1$–$C_4$-halogenoalkylthio having 1 to 5 halogen atoms, aminocarbonyl, or aminocarbonyl-$C_1$–$C_4$-alkyl and
$R^2$ represents fluorine and
$R^3$ represents hydrogen, $C_2$–$C_4$-alkyl, $C_1$–$C_4$-halogenoalkyl having 1 to 5 halogen atoms, hydroxy-$C_1$–$C_4$-alkyl, $C_2$–$C_6$-alkenyl, $C_3$–$C_6$-cycloalkyl, $C_1$–$C_4$-alkylthio-$C_1$–$C_4$-alkyl, $C_1$–$C_4$-halogenoalkylthio-$C_1$–$C_4$-alkyl having 1 to 5 halogen atoms, $C_1$–$C_4$-alkoxy-$C_1$–$C_4$-alkyl, $C_1$–$C_4$-halogenoalkoxy-$C_1$–$C_4$-alkyl having 1 to 5 halogen atoms or phenyl, or
A represents a radical of the formula

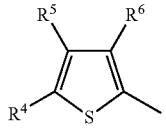

in which
$R^4$ and $R^5$ independently of one another each represent hydrogen, halogen, $C_1$–$C_4$-alkyl or $C_1$–$C_4$-halogenoalkyl having 1 to 5 halogen atoms and
$R^6$ represents halogen, cyano or $C_1$–$C_4$-alkyl or $C_1$–$C_4$-halogenoalkoxy having 1 to 5 halogen atoms, or
A represents a radical of the formula

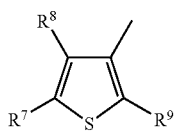

in which
$R^7$ and $R^8$ independently of one another each represent hydrogen, halogen, $C_1$–$C_4$-alkyl or $C_1$–$C_4$-halogenoalkyl having 1 to 5 halogen atoms and $R^9$ represents hydrogen, $C_1-C_4$-alkyl or represents halogen, or A represents a radical of the formula

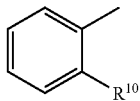

in which
$R^{10}$ represents hydrogen, halogen, hydroxy, cyano, $C_1-C_6$-alkyl, $C_1-C_4$-halogenoalkyl having 1 to 5 halogen atoms, $C_1-C_4$-halogenoalkoxy having 1 to 5 halogen atoms or represents $C_1-C_4$-halogenoalkylthio having 1 to 5 halogen atoms, or A represents a radical of the formula

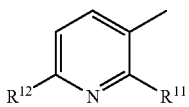

in which
$R^{11}$ represents halogen, hydroxy, cyano, $C_1-C_4$-alkyl, $C_1-C_4$-halogenoalkyl having 1 to 5 halogen atoms, $C_1-C_4$-alkoxy, $C_1-C_4$-alkylthio, $C_1-C_4$-halogenoalkylthio having 1 to 5 halogen atoms, or represents $C_1-C_4$-halogenoalkoxy having 1 to 5 halogen atoms and $R^{12}$ represents hydrogen, halogen, cyano, $C_1-C_4$-alkyl, $C_1-C_4$-halogenoalkyl having 1 to 5 halogen atoms, $C_1-C_4$-alkoxy, $C_1-C_4$-alkylthio, $C_1-C_4$-halogenoalkoxy having 1 to 5 halogen atoms, $C_1-C_4$-alkylsulphinyl or represents $C_1-C_4$-alkylsulphonyl, or A represents a radical of the formula

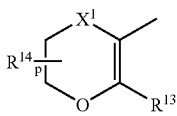

in which
$R^{13}$ represents $C_1-C_4$-alkyl or represents $C_1-C_4$-halogenoalkyl having 1 to 5 halogen atoms and $R^{14}$ represents $C_1-C_4$-alkyl, $X^1$ represents a sulphur atom, represents SO, $SO_2$ or $CH_2$, p represents 0, 1 or 2, or A represents a radical of the formula

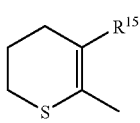

in which
$R^{15}$ represents $C_1-C_4$-alkyl or represents $C_1-C_4$-halogenoalkyl having 1 to 5 halogen atoms, or A represents a radical of the formula

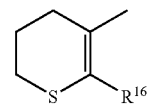

in which
$R^{16}$ represents $C_1-C_4$-alkyl or represents $C_1-C_4$-halogenoalkyl having 1 to 5 halogen atoms, or A represents a radical of the formula

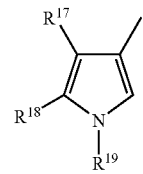

in which
$R^{17}$ represents halogen, cyano, $C_1-C_4$-alkyl or represents $C_1-C_4$-halogenoalkyl having 1 to 5 halogen atoms and $R^{18}$ represents hydrogen, halogen, $C_1-C_4$-alkyl or represents $C_1-C_4$-halogenoalkyl having 1 to 5 halogen atoms, $R^{19}$ represents hydrogen, cyano, $C_1-C_4$-alkyl, $C_1-C_4$-halogenoalkyl having 1 to 5 halogen atoms, $C_1-C_4$-alkoxy-$C_1-C_4$-alkyl, hydroxy-$C_1-C_4$-alkyl, $C_1-C_4$-alkylsulphonyl, di($C_1-C_4$-alkyl)aminosulphonyl, $C_1-C_6$-alkylcarbonyl or represents optionally substituted phenylsulphonyl or benzoyl, or A represents a radical of the formula

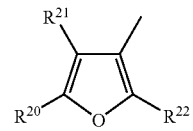

in which
$R^{20}$ and $R^{21}$ independently of one another each represent hydrogen, halogen, amino, $C_1-C_4$-alkyl or represent $C_1-C_4$-halogenoalkyl having 1 to 5 halogen atoms and $R^{22}$ represents hydrogen, halogen, $C_1-C_4$-alkyl or represents $C_1-C_4$-halogenoalkyl having 1 to 5 halogen atoms, or A represents a radical of the formula

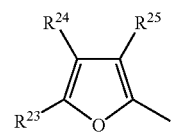

in which
$R^{23}$ and $R^{24}$ independently of one another each represent hydrogen, halogen, amino, nitro, $C_1-C_4$-alkyl or represent $C_1-C_4$-halogenoalkyl having 1 to 5 halogen atoms and $R^{25}$ represents hydrogen, halogen, $C_1-C_4$-alkyl or represents $C_1-C_4$-halogenoalkyl having 1 to 5 halogen atoms, or A represents a radical of the formula

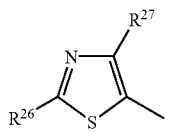

in which
R²⁶ represents hydrogen, halogen, amino, $C_1$–$C_4$-alkylamino, di-($C_1$–$C_4$-alkyl)amino, cyano, $C_1$–$C_4$-alkyl or represents $C_1$–$C_4$-halogenoalkyl having 1 to 5 halogen atoms and
R²⁷ represents halogen, $C_1$–$C_4$-alkyl or $C_1$–$C_4$-halogenoalkyl having 1 to 5 halogen atoms, or
A represents a radical of the formula

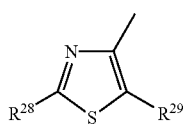

in which
R²⁸ represents hydrogen, halogen, amino, $C_1$–$C_4$-alkylamino, di-($C_1$–$C_4$-alkyl)amino, cyano, $C_1$–$C_4$-alkyl or represents $C_1$–$C_4$-halogenoalkyl having 1 to 5 halogen atoms and
R²⁹ represents halogen, $C_1$–$C_4$-alkyl or $C_1$–$C_4$-halogenoalkyl having 1 to 5 halogen atoms, or
A represents a radical of the formula

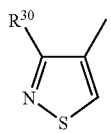

in which
R³⁰ represents halogen, $C_1$–$C_4$-alkyl or $C_1$–$C_4$-halogenoalkyl having 1 to 5 halogen atoms, or
A represents a radical of the formula

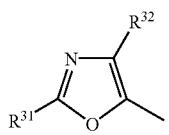

in which
R³¹ represents hydrogen or $C_1$–$C_4$-alkyl and
R³² represents halogen or $C_1$–$C_4$-alkyl, or
A represents a radical of the formula

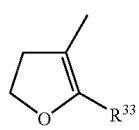

in which
R³³ represents $C_1$–$C_4$-alkyl or $C_1$–$C_4$-halogenoalkyl having 1 to 5 halogen atoms, or
A represents a radical of the formula

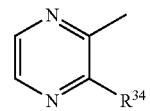

in which
R³⁴ represents hydrogen, halogen or represents $C_1$–$C_4$-alkyl, have now been found.

Furthermore, it has been found that biphenylcarboxamides of the formula (I) are obtained when
a) carboxylic acid derivatives of the formula (II)

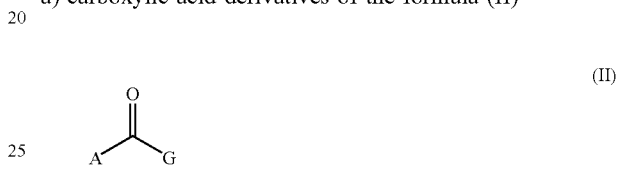

(II)

in which
A is as defined above and
G represents halogen, hydroxy or $C_1$–$C_6$-alkoxy,
are reacted with aniline derivatives of the formula (III)

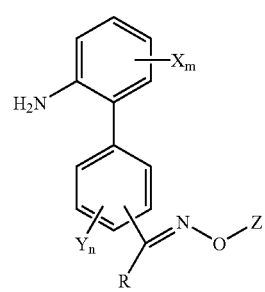

(III)

in which
R, Z, X, Y, m and n are each as defined above,
if appropriate in the presence of a catalyst, if appropriate in the presence of an acid binder and if appropriate in the presence of a diluent, or
b) carboxamide derivatives of the formula (IV)

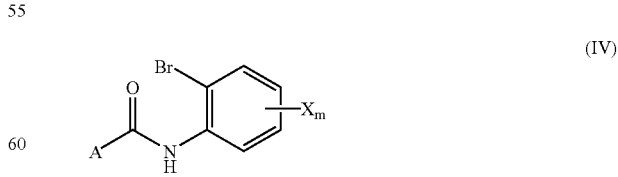

(IV)

in which
A, X and m are each as defined above,
are reacted with boronic acid derivatives of the formula (V)

d) biphenylacyl derivatives of the formula (VIII)

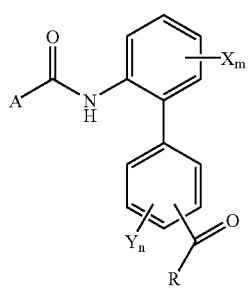
(VIII)

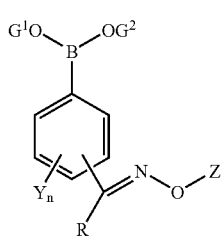
(V)

in which
R, Z, Y and n are each as defined above and
G¹ and G² each represent hydrogen or together represent tetramethylethylene,
in the presence of a catalyst, if appropriate in the presence of an acid binder and if appropriate in the presence of a diluent, or c) carboxamide-boronic acid derivatives of the formula (VI)

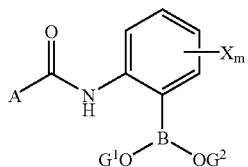
(VI)

in which
A, X and m are each as defined above and
G¹ and G² each represent hydrogen or together represent tetramethylethylene,
are reacted with phenyloxime derivatives of the formula (VII)

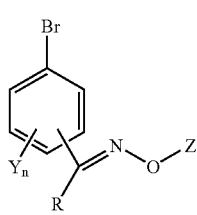
(VII)

in which
R, Z, Y and n are each as defined above,
in the presence of a catalyst, if appropriate in the presence of an acid binder and if appropriate in the presence of a diluent, or in which
A, R, X, Y, m and n are each as defined above,
are reacted with alkoxamines of the formula (IX)

$$Z-O-NH_2 \times HCl \quad (IX)$$

in which Z is as defined above,
if appropriate in the presence of an acid binder and if appropriate in the presence of a diluent, or e) hydroxyamine derivatives of the formula (I-a)

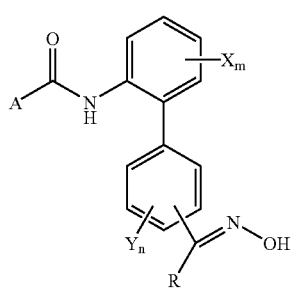
(I-a)

in which
A, R, X, Y, m and n are each as defined above,
are reacted with compounds of the formula (X)

$$Z^1-E \quad (X)$$

in which
$Z^1$ represents $C_1$–$C_6$-alkyl and
E represents chlorine, bromine, iodine, methanesulphonyl or p-toluene-sulphonyl, or
$Z^1$ and E together represent di-$C_1$–$C_6$-alkyl sulphate,
if appropriate in the presence of an acid binder and if appropriate in the presence of a diluent, or f) carboxamide derivatives of the formula (IV)

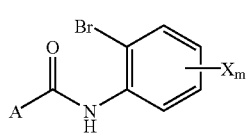
(IV)

in which
A, X and m are each as defined above,
are reacted with phenyloxime derivatives of the formula (VII)

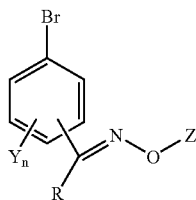

(VII)

in which

R, Z, Y and n are each as defined above, in the presence of a palladium or platinum catalyst and in the presence of 4,4,4',4',5,5,5',5'-octamethyl-2,2'-bis-1,3,2-dioxaborolane, if appropriate in the presence of an acid binder and if appropriate in the presence of a diluent.

Finally, it has been found that the novel biphenylcarboxamides of the formula (I) have very good microbicidal properties and can be used for controlling undesirable microorganisms both in crop protection and in the protection of materials.

Surprisingly, the biphenylcarboxamides of the formula (I) according to the invention have considerably better fungicidal activity than the active prior-art compounds of the most similar constitution and the same direction of action.

The formula (I) provides a general definition of the biphenylcarboxamides according to the invention.

R preferably represents hydrogen, $C_1$–$C_4$-alkyl, $C_3$–$C_6$-cycloalkyl or $C_1$–$C_4$-halogenoalkyl having 1 to 5 halogen atoms.

Z preferably represents hydrogen, $C_1$–$C_4$-alkyl or $C_1$–$C_4$-halogenoalkyl having 1 to 5 halogen atoms.

X and Y independently of one another each preferably represent fluorine, chlorine, bromine, nitro, cyano, hydroxy, carboxyl, $C_1$–$C_6$-alkyl, $C_1$–$C_2$-halogenoalkyl having 1 to 5 fluorine, chlorine and/or bromine atoms, $C_1$–$C_6$-alkoxy, $C_1$–$C_2$-halogenoalkoxy having 1 to 5 fluorine, chlorine and/or bromine atoms, $C_1$–$C_6$-alkylthio, $C_1$–$C_2$-halogenoalkylthio having 1 to 5 fluorine, chlorine and/or bromine atoms, $C_2$–$C_6$-alkenyloxy, $C_2$–$C_6$-halogenoalkenyloxy having 1 to 5 halogen atoms, $C_3$–$C_6$-alkinyloxy, $C_3$–$C_6$-halogenoalkinyloxy having 1 to 5 halogen atoms, $C_3$–$C_7$-cycloalkyl, $C_1$–$C_4$-alkoxycarbonyl, $C_1$–$C_6$-alkylsulphinyl, $C_1$–$C_6$-alkylsulphonyl, $C_1$–$C_6$-halogenoalkylsulphinyl having 1 to 5 halogen atoms, $C_1$–$C_6$-halogenoalkylsulphonyl having 1 to 5 halogen atoms or represents $C_1$–$C_4$-alkoximino-$C_1$–$C_4$-alkyl.

m preferably represents integers from 0 to 3, where X represents identical or different radicals if m represents 2 or 3.

n preferably represents integers from 0 to 4, where Y represents identical or different radicals if n represents 2, 3 or 4.

A preferably represents a radical of the formula in which

α) $R^1$ represents hydrogen, cyano, fluorine, chlorine, bromine, iodine methyl, ethyl, isopropyl, $C_1$–$C_2$-halogenoalkyl having 1 to 5 fluorine, chlorine and/or bromine atoms, cyclopropyl, methoxy, ethoxy, $C_1$–$C_2$-halogenoalkoxy having 1 to 5 fluorine, chlorine and/or bromine atoms, methylthio, ethylthio, trifluoromethylthio, difluoromethylthio, aminocarbonyl, aminocarbonylmethyl or aminocarbonylethyl, $R^2$ represents hydrogen, chlorine, bromine, iodine, methyl, ethyl, methoxy, ethoxy, methylthio or ethylthio and $R^3$ represents hydrogen, methyl, ethyl, n-propyl, isopropyl, $C_1$–$C_2$-halogenoalkyl having 1 to 5 fluorine, chlorine and/or bromine atoms, hydroxymethyl, hydroxyethyl, cyclopropyl, cyclopentyl, cyclohexyl or phenyl, or β) $R^1$ represents hydrogen, cyano, fluorine, chlorine, bromine, iodine, ethyl, isopropyl, $C_1$–$C_2$-halogenoalkyl having 1 to 5 fluorine, chlorine and/or bromine atoms, cyclopropyl, methoxy, ethoxy, $C_1$–$C_2$-halogenoalkoxy having 1 to 5 fluorine, chlorine and/or bromine atoms, methylthio, ethylthio, trifluoromethylthio, difluoromethylthio, aminocarbonyl, aminocarbonylmethyl or aminocarbonylethyl, $R^2$ represents fluorine and $R^3$ represents hydrogen, methyl, ethyl, n-propyl, isopropyl, $C_1$–$C_2$-halogenoalkyl having 1 to 5 fluorine, chlorine and/or bromine atoms, hydroxymethyl, hydroxyethyl, cyclopropyl, cyclopentyl, cyclohexyl or phenyl, or γ) $R^1$ represents hydrogen, cyano, fluorine, chlorine, bromine, iodine, methyl, ethyl, isopropyl, $C_1$–$C_2$-halogenoalkyl having 1 to 5 fluorine, chlorine and/or bromine atoms, cyclopropyl, methoxy, ethoxy, $C_1$–$C_2$-halogenoalkoxy having 1 to 5 fluorine, chlorine and/or bromine atoms, methylthio, ethylthio, trifluoromethylthio, difluoromethylthio, aminocarbonyl, aminocarbonylmethyl or aminocarbonylethyl, $R^2$ represents fluorine and $R^3$ represents hydrogen, ethyl, n-propyl, isopropyl, $C_1$–$C_2$-halogenoalkyl having 1 to 5 fluorine, chlorine and/or bromine atoms, hydroxymethyl, hydroxyethyl, cyclopropyl, cyclopentyl, cyclohexyl or phenyl.

A furthermore preferably represents a radical of the formula

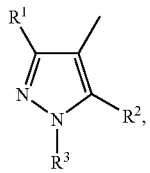

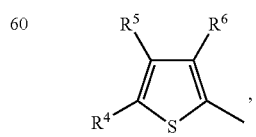

in which
R$^4$ and R$^5$ independently of one another each represent hydrogen, fluorine, chlorine, bromine, methyl, ethyl or C$_1$–C$_2$-halogenoalkyl having 1 to 5 fluorine, chlorine and/or bromine atoms and R$^6$ represents fluorine, chlorine, bromine, cyano, methyl, ethyl or C$_1$–C$_2$-halogenoalkoxy having 1 to 5 fluorine, chlorine and/or bromine atoms.

A furthermore preferably represents a radical of the formula

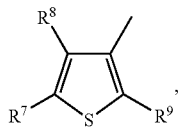

in which
R$^7$ and R$^8$ independently of one another each represent hydrogen, fluorine, chlorine, bromine, methyl, ethyl or C$_1$–C$_2$-halogenoalkyl having 1 to 5 fluorine, chlorine and/or bromine atoms and R$^9$ represents hydrogen, fluorine, chlorine, bromine, methyl or ethyl.

A furthermore preferably represents a radical of the formula

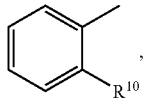

in which
R$^{10}$ represents hydrogen, fluorine, chlorine, bromine, iodine, hydroxy, cyano, C$_1$–C$_4$-alkyl, C$_1$–C$_2$-halogenoalkyl having 1 to 5 fluorine, chlorine and/or bromine atoms, C$_1$–C$_2$-halogenoalkoxy having 1 to 5 fluorine, chlorine and/or bromine atoms or represents C$_1$–C$_2$-halogenoalkylthio having 1 to 5 fluorine, chlorine and/or bromine atoms.

A furthermore preferably represents a radical of the formula

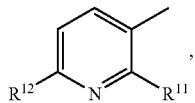

in which
R$^{11}$ represents fluorine, chlorine, bromine, iodine, hydroxy, cyano, C$_1$–C$_4$-alkyl, C$_1$–C$_2$-halogenoalkyl having 1 to 5 fluorine, chlorine and/or bromine atoms, methoxy, ethoxy, methylthio, ethylthio, difluoromethylthio, trifluoromethylthio, or represents C$_1$–C$_2$-halogenoalkoxy having 1 to 5 fluorine, chlorine and/or bromine atoms and R$^{12}$ represents hydrogen, fluorine, chlorine, bromine, iodine, cyano, C$_1$–C$_4$-alkyl, C$_1$–C$_2$-halogenoalkyl having 1 to 5 fluorine, chlorine and/or bromine atoms, methoxy, ethoxy, methylthio, ethylthio, represents C$_1$–C$_2$-halogenoalkoxy having 1 to 5 fluorine, chlorine and/or bromine atoms, C$_1$–C$_2$-alkylsulphinyl or C$_1$–C$_2$-alkylsulphonyl.

A furthermore preferably represents a radical of the formula

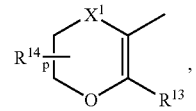

in which
R$^{13}$ represents methyl, ethyl or represents C$_1$–C$_2$-halogenoalkyl having 1 to 5 fluorine, chlorine and/or bromine atoms and R$^{14}$ represents methyl or ethyl, X$^1$ represents a sulphur atom, represents SO, SO$_2$ or CH$_2$ and p represents 0, 1 or 2.

A furthermore preferably represents a radical of the formula

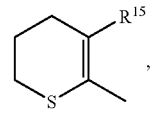

in which
R$^{15}$ represents methyl, ethyl or represents C$_1$–C$_2$-halogenoalkyl having 1 to 5 fluorine, chlorine and/or bromine atoms.

A furthermore preferably represents a radical of the formula

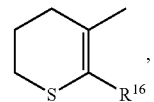

in which
R$^{16}$ represents methyl, ethyl or represents C$_1$–C$_2$-halogenoalkyl having 1 to 5 fluorine, chlorine and/or bromine atoms.

A furthermore preferably represents a radical of the formula

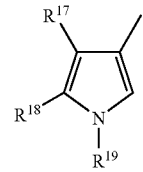

in which
R$^{17}$ represents fluorine, chlorine, bromine, cyano, methyl, ethyl, isopropyl or represents C$_1$–C$_2$-halogenoalkyl having 1 to 5 fluorine, chlorine and/or bromine atoms, R$^{18}$ represents hydrogen, fluorine, chlorine, bromine, methyl, ethyl or represents C$_1$–C$_2$-halogenoalkyl having 1 to 5 fluorine, chlorine and/or bromine atoms and R$^{19}$ represents hydrogen, methyl, ethyl, C$_1$–C$_2$-halogenoalkyl having 1 to 5 fluorine, chlorine and/or bromine atoms, C$_1$–C$_2$-alkoxy-C$_1$–C$_2$-alkyl, hydroxymethyl, hydroxyethyl, methylsulphonyl or dimethylaminosulphonyl.

A furthermore preferably represents a radical of the formula

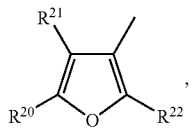

in which
R²⁰ and R²¹ independently of one another each represent hydrogen, fluorine, chlorine, bromine, amino, methyl, ethyl or represent $C_1$–$C_2$-halogenoalkyl having 1 to 5 fluorine, chlorine and/or bromine atoms and
R²² represents hydrogen, fluorine, chlorine, bromine, methyl, ethyl or represents $C_1$–$C_2$-halogenoalkyl having 1 to 5 fluorine, chlorine and/or bromine atoms.

A furthermore preferably represents a radical of the formula

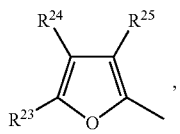

in which
R²³ and R²⁴ independently of one another each represent hydrogen, fluorine, chlorine, bromine, amino, nitro, methyl, ethyl or represent $C_1$–$C_2$-halogenoalkyl having 1 to 5 fluorine, chlorine and/or bromine atoms and
R²⁵ represents hydrogen, fluorine, chlorine, bromine, methyl, ethyl or represents $C_1$–$C_2$-halogenoalkyl having 1 to 5 fluorine, chlorine and/or bromine atoms.

A furthermore preferably represents a radical of the formula

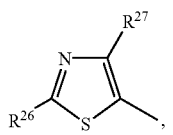

in which
R²⁶ represents hydrogen, fluorine, chlorine, bromine, amino, $C_1$–$C_4$-alkylamino, di-($C_1$–$C_4$-alkyl)amino, cyano, methyl, ethyl or represents $C_1$–$C_2$-halogenoalkyl having 1 to 5 fluorine, chlorine and/or bromine atoms and
R²⁷ represents fluorine, chlorine, bromine, methyl, ethyl or $C_1$–$C_2$-halogenoalkyl having 1 to 5 fluorine, chlorine and/or bromine atoms.

A furthermore preferably represents a radical of the formula

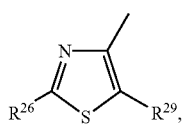

in which
R²⁸ represents hydrogen, fluorine, chlorine, bromine, amino, $C_1$–$C_4$-alkylamino, di-($C_1$–$C_4$-alkyl)amino, cyano, methyl, ethyl or represents $C_1$–$C_2$-halogenoalkyl having 1 to 5 fluorine, chlorine and/or bromine atoms and
R²⁹ represents fluorine, chlorine, bromine, methyl, ethyl or $C_1$–$C_2$-halogenoalkyl having 1 to 5 fluorine, chlorine and/or bromine atoms.

A furthermore preferably represents a radical of the formula

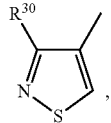

in which
R³⁰ represents fluorine, chlorine, bromine, methyl, ethyl or $C_1$–$C_2$-halogenoalkyl having 1 to 5 fluorine, chlorine and/or bromine atoms.

A furthermore preferably represents a radical of the formula

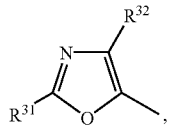

in which
R³¹ represents hydrogen, methyl or ethyl and
R³² represents fluorine, chlorine, bromine, methyl or ethyl.

A furthermore preferably represents a radical of the formula

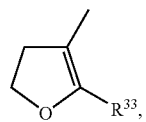

in which
R³³ represents methyl, ethyl or $C_1$–$C_2$-halogenoalkyl having 1 to 5 fluorine, chlorine and/or bromine atoms.

A furthermore preferably represents a radical of the formula

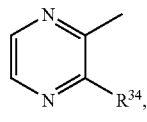

in which
R³⁴ represents hydrogen, fluorine, chlorine, bromine, methyl or ethyl.

R particularly preferably represents hydrogen, $C_1$–$C_4$-alkyl.
Z particularly preferably represents hydrogen, $C_1$–$C_4$-alkyl.
X and Y independently of one another each particularly preferably represent fluorine, chlorine, bromine, nitro, cyano, hydroxy, carboxyl, methyl, ethyl, n-propyl, isopropyl, n-butyl, sec-butyl, i-butyl, tert-butyl, trichloromethyl, trifluoromethyl, difluoromethyl, difluorochloromethyl, methoxy, ethoxy, difluoromethoxy, trifluoromethoxy, methylthio, trifluoromethylthio, difluorochloromethylthio, allyloxy, propargyloxy, cyclopropyl, cyclopentyl, cyclohexyl, cycloheptyl, methoxycarbonyl, ethoxycarbonyl, methoximinomethyl, ethoximinoethyl, methoximinomethyl or ethoximinoethyl.

m particularly preferably represents integers from 0 to 3, where X represents identical or different radicals if m represents 2 or 3.

n particularly preferably represents the numbers 0 to 4, where Y represents identical or different radicals if n represents 2, 3 or 4.

A particularly preferably represents a radical of the formula

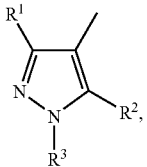

in which
α) $R^1$ represents hydrogen, fluorine, chlorine, bromine, iodine, methyl, ethyl, isopropyl, monofluoromethyl, difluoromethyl, trifluoromethyl, difluorochloromethyl, trichloromethyl, cyclopropyl, methoxy, ethoxy, trifluoromethoxy, trichloromethoxy, methylthio, ethylthio, trifluoromethylthio or difluoromethylthio and
$R^2$ represents hydrogen, chlorine, bromine, iodine, methyl, ethyl, methoxy, ethoxy, methylthio or ethylthio and
$R^3$ represents hydrogen, methyl, ethyl, trifluoromethyl, difluoromethyl, hydroxymethyl, hydroxyethyl or phenyl, or
β) $R^1$ represents hydrogen, fluorine, chlorine, bromine, iodine, ethyl, isopropyl, monofluoromethyl, difluoromethyl, trifluoromethyl, difluorochloromethyl, trichloromethyl, cyclopropyl, methoxy, ethoxy, trifluoromethoxy, trichloromethoxy, methylthio, ethylthio, trifluoromethylthio or difluoromethylthio and
$R^2$ represents fluorine and
$R^3$ represents hydrogen, methyl, ethyl, trifluoromethyl, difluoromethyl, hydroxymethyl, hydroxyethyl or phenyl, or
γ) $R^1$ represents hydrogen, fluorine, chlorine, bromine, iodine, methyl, ethyl, isopropyl, monofluoromethyl, difluoromethyl, trifluoromethyl, difluorochloromethyl, trichloromethyl, cyclopropyl, methoxy, ethoxy, trifluoromethoxy, trichloromethoxy, methylthio, ethylthio, trifluoromethylthio or difluoromethylthio and
$R^2$ represents fluorine and
$R^3$ represents hydrogen, ethyl, trifluoromethyl, difluoromethyl, hydroxymethyl, hydroxyethyl or phenyl.

A furthermore particularly preferably represents a radical of the formula

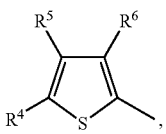

in which
$R^4$ and $R^5$ independently of one another each represent hydrogen, fluorine, chlorine, bromine, methyl, ethyl, difluoromethyl, trifluoromethyl, difluorochloromethyl or trichloromethyl and $R^6$ represents fluorine, chlorine, bromine, cyano, methyl, trifluoromethoxy, difluoromethoxy, difluorochloromethoxy or trichloromethoxy.

A furthermore particularly preferably represents a radical of the formula

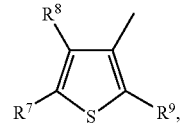

in which
$R^7$ and $R^8$ independently of one another each represent hydrogen, fluorine, chlorine, bromine, methyl, ethyl, difluoromethyl, trifluoromethyl, difluorochloromethyl or trichloromethyl and
$R^9$ represents hydrogen, fluorine, chlorine, bromine, methyl or ethyl.

A furthermore particularly preferably represents a radical of the formula

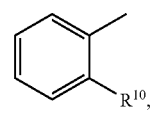

in which
$R^{10}$ represents hydrogen, fluorine, chlorine, bromine, iodine hydroxy, cyano, methyl, ethyl, n-propyl, isopropyl, n-butyl, i-butyl, sec-butyl, tert-butyl, difluoromethyl, trifluoromethyl, difluorochloromethyl, trichloromethyl, trifluoromethoxy, difluoromethoxy, difluorochloromethoxy, trichloromethoxy, trifluoromethylthio, difluoromethylthio, difluorochloromethylthio or trichloromethylthio.

A furthermore particularly preferably represents a radical of the formula

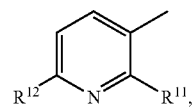

in which
$R^{11}$ represents fluorine, chlorine, bromine, iodine hydroxy, cyano, methyl, ethyl, n-propyl, isopropyl, n-butyl, i-butyl, sec-butyl, tert-butyl, trifluoromethyl, difluoromethyl, difluorochloromethyl, trichloromethyl, methoxy, ethoxy, methylthio, ethylthio, difluoromethylthio, trifluoromethylthio, trifluoromethoxy, difluoromethoxy, difluorochloromethoxy or trichloromethoxy and
$R^{12}$ represents hydrogen, fluorine, chlorine, bromine, iodine, cyano, n-propyl, isopropyl, n-butyl, i-butyl, sec-butyl, tert-butyl, trifluoromethyl, difluoromethyl, difluorochloromethyl, trichloromethyl, methoxy, ethoxy, methylthio, ethylthio, trifluoromethoxy, difluoromethoxy, difluorochloromethoxy, trichloromethoxy, methylsulphinyl or methylsulphonyl.

A furthermore particularly preferably represents a radical of the formula

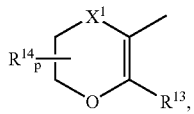

in which
R$^{13}$ represents methyl, ethyl, trifluoromethyl, difluoromethyl, difluorochloromethyl or trichloromethyl and
R$^{14}$ represents methyl or ethyl,
X$^1$ represents a sulphur atom, represents SO, SO$_2$ or CH$_2$ and
p represents 0, 1 or 2.

A furthermore particularly preferably represents a radical of the formula

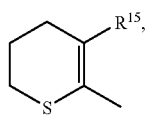

in which
R$^{15}$ represents methyl, ethyl, trifluoromethyl, difluoromethyl, difluorochloromethyl or trichloromethyl.

A furthermore particularly preferably represents a radical of the formula

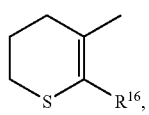

in which
R$^{16}$ represents methyl, ethyl, trifluoromethyl, difluoromethyl, difluorochloromethyl or trichloromethyl.

A furthermore particularly preferably represents a radical of the formula

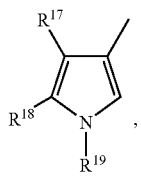

in which
R$^{17}$ represents fluorine, chlorine, bromine, cyano, methyl, ethyl, isopropyl, trifluoromethyl, difluoromethyl, difluorochloromethyl or trichloromethyl,
R$^{18}$ represents hydrogen, fluorine, chlorine, bromine, methyl, ethyl, trifluoromethyl, difluoromethyl or trichloromethyl and
R$^{19}$ hydrogen, methyl, ethyl, trifluoromethyl, methoxymethyl, ethoxymethyl, hydroxymethyl or hydroxyethyl.

A furthermore particularly preferably represents a radical of the formula

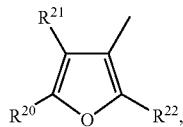

in which
R$^{20}$ and R$^{21}$ independently of one another each represent hydrogen, fluorine, chlorine, bromine, methyl, ethyl, trifluoromethyl, difluoromethyl, difluorochloromethyl or trichloromethyl and
R$^{22}$ represents hydrogen, fluorine, chlorine, bromine, methyl, ethyl, trifluoromethyl, difluoromethyl, difluorochloromethyl or trichloromethyl.

A furthermore particularly preferably represents a radical of the formula

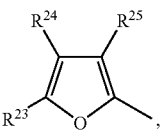

in which
R$^{23}$ and R$^{24}$ independently of one another each represent hydrogen, fluorine, chlorine, bromine, nitro, methyl, ethyl, trifluoromethyl, difluoromethyl, difluorochloromethyl or trichloromethyl and
R$^{25}$ represents hydrogen, fluorine, chlorine, bromine, methyl, ethyl, trifluoromethyl, difluoromethyl, difluorochloromethyl or trichloromethyl.

A furthermore particularly preferably represents a radical of the formula

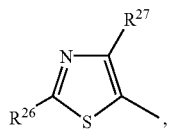

in which
R$^{26}$ represents hydrogen, fluorine, chlorine, bromine, amino, methylamino, dimethylamino, cyano, methyl, ethyl, trifluoromethyl, difluoromethyl, difluorochloromethyl or trichloromethyl and
R$^{27}$ represents fluorine, chlorine, bromine, methyl, ethyl, trifluoromethyl, difluoromethyl, difluorochloromethyl or trichloromethyl.

A furthermore particularly preferably represents a radical of the formula

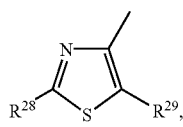

in which
R$^{28}$ represents hydrogen, fluorine, chlorine, bromine, amino, methylamino, dimethylamino, cyano, methyl, ethyl, trifluoromethyl, difluoromethyl, difluorochloromethyl or trichloromethyl and $R^{29}$ represents fluorine, chlorine, bromine, methyl, ethyl, trifluoromethyl, difluoromethyl, difluorochloromethyl or trichloromethyl.

A furthermore particularly preferably represents a radical of the formula

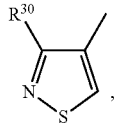

in which $R^{30}$ represents fluorine, chlorine, bromine, methyl, ethyl, trifluoromethyl, difluoromethyl, difluorochloromethyl or trichloromethyl.

A furthermore particularly preferably represents a radical of the formula

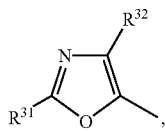

in which $R^{31}$ represents hydrogen, methyl or ethyl and $R^{32}$ represents fluorine, chlorine, bromine, methyl or ethyl.

A furthermore particularly preferably represents a radical of the formula

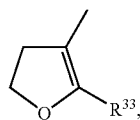

in which $R^{33}$ represents methyl, ethyl, trifluoromethyl, difluoromethyl, difluorochloromethyl or trichloromethyl.

A furthermore particularly preferably represents a radical of the formula

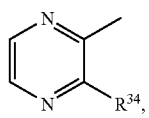

in which $R^{34}$ represents hydrogen, fluorine, chlorine, bromine, methyl or ethyl.

Preference or particular preference is given to compounds which carry the substituents mentioned under preferred or particularly preferred.

Saturated or unsaturated hydrocarbon radicals, such as alkyl or alkenyl, can in each case be straight-chain or branched as far as this is possible, including in combination with heteroatoms, such as, for example, in alkoxy.

Optionally substituted radicals can be mono- or polysubstituted, where in the case of polysubstitution the substituents can be identical or different. A plurality of radicals having the same indices, such as, for example, m radicals X for m>1, can be identical or different.

Halogen-substituted radicals, such as, for example, halogenoalkyl, are mono- or polyhalogenated. In the case of polyhalogenation, the halogen atoms can be identical or different. Here, halogen represents fluorine, chlorine, bromine and iodine, in particular fluorine, chlorine and bromine.

However, the above-mentioned general or preferred radical definitions or illustrations can also be combined with one another as desired, i.e. including combinations between the respective ranges and preferred ranges. The definitions apply to the end products and, correspondingly, to the precursors and intermediates. Moreover, individual definitions may also not apply.

Using 2-methyl-4-trifluoromethyl-1,3-thiazole-5-carbonyl chloride and 2-(4-methoximinomethyl-phenyl)aniline as starting materials, the course of the process (a) according to the invention can be illustrated by the equation below.

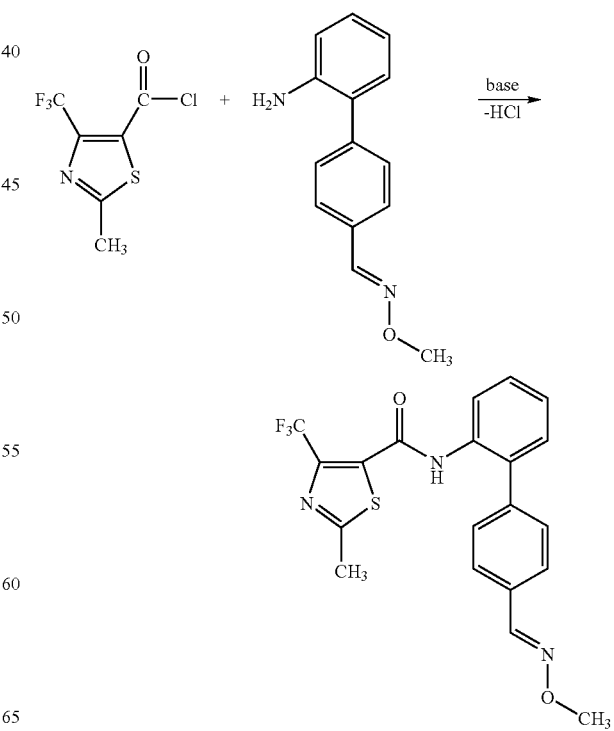

Using 2'-bromo-1,3-dimethylpyrrole-4-carboxanilide and 4-methoximinoethylphenyl-boronic acid as starting materials and a catalyst, the course of the process (b) according to the invention can be illustrated by the equation below.

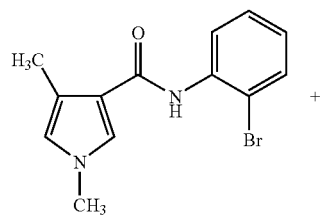

+

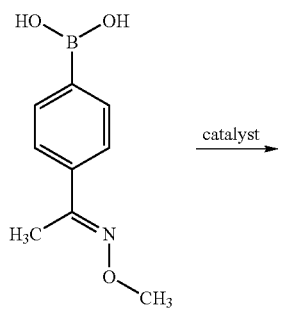

Using 2-[(1,4-dimethylpyrrol-3-yl)carbonylamino]phenyl-boronic acid and 1-bromo-4-methoximinoethyl-benzene as starting materials and a catalyst, the course of the process (c) according to the invention can be illustrated by the equation below.

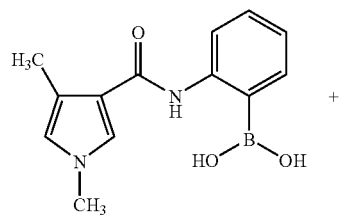

+

-continued

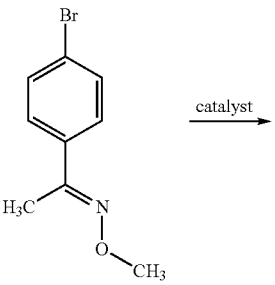

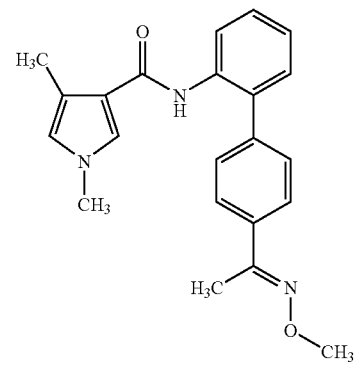

Using 2'-(4-acetyl-phenyl)-4'-fluoro-1-methyl-3-trifluoromethylpyrazole-4-carboxanilide and methoxamine hydrochloride as starting materials, the course of the process (d) according to the invention can be illustrated by the equation below.

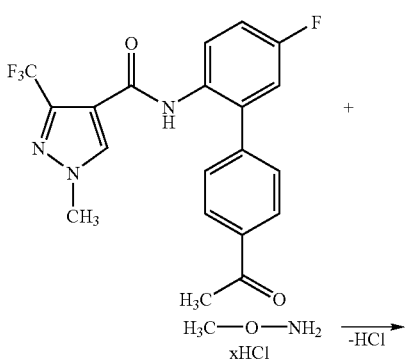

+

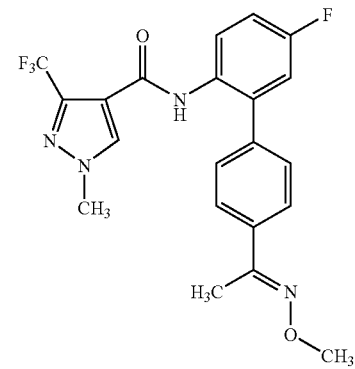

Using 2'-(4-hydroximinoethyl)-phenyl-1,3-dimethylpyrazole-4-carboxanilide and methylbromide as starting materials, the course of the process (e) according to the invention can be illustrated by the equation below.

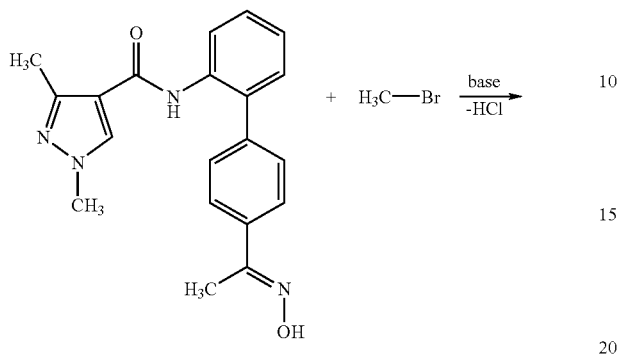

Using 2'-bromo-5-fluorothiazole-4-carboxanilide and 1-bromo-4-methoximinomethyl-methyl-benzene as starting materials and a catalyst and 4,4,4',4',5,5,5',5'-octamethyl-2,2'-bis-1,3,2-dioxaborolane, the course of the process (f) according to the invention can be illustrated by the equation below.

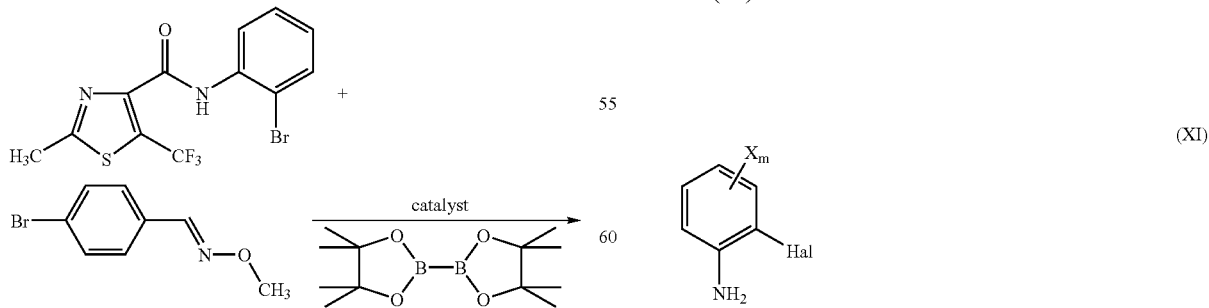

-continued

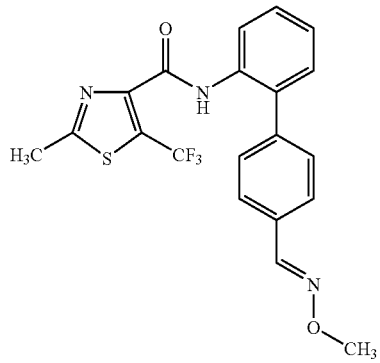

Illustration of the Processes and Intermediates

The formula (II) provides a general definition of the carboxylic acid derivatives required as starting materials for carrying out the process (a) according to the invention. In this formula, A preferably has those meanings which have already been mentioned in connection with the description of the substances of the formula (I) according to the invention as being preferred or particularly preferred for these radicals. G preferably represents chlorine, bromine, hydroxy, methoxy or ethoxy, particularly preferably chlorine, hydroxy or methoxy.

The carboxylic acid derivatives of the formula (II) are known or can be prepared by known processes (cf. WO 93/11 117, EP-A 0 545 099, EP-A 0 589 301 and EP-A 0 589 313).

The formula (III) provides a general definition of the aniline derivatives required as reaction components for carrying out the process (a) according to the invention. In this formula, R, Z, X, Y, m and n each preferably have those meanings which have already been mentioned in connection with the description of the substances of the formula (I) according to the invention as being preferred or being particularly preferred for these radicals or indices.

The aniline derivatives of the formula (III) are novel. Some of them can be prepared by known methods (cf. EP-A 0 545 099 and EP-A 0 589 301). The aniline derivatives of the formula (III) are furthermore obtained by g) reacting 2-halogenaniline derivatives of the general formula (XI)

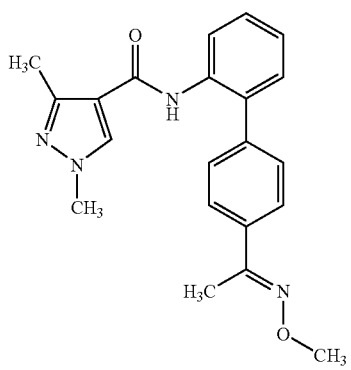

(XI)

in which

X and m are each as defined above and

Hal represents halogen with boronic acid derivatives of the formula (V)

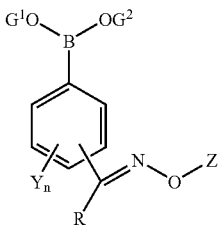

(V)

in which

R, Z, Y, n, $G^1$ and $G^2$ are each as defined above, if appropriate in the presence of an acid binder, and if appropriate in the presence of an inert organic diluent, and if appropriate in the presence of a catalyst, or h) by reacting anilineboronic acids of the formula (XII)

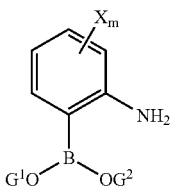

(XII)

in which

X, m, $G^1$ and $G^2$ are each as defined above with phenyloxime derivatives of the formula (VII)

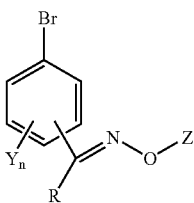

(VII)

in which

R, Z, Y and n are each as defined above, if appropriate in the presence of an acid binder, and if appropriate in the presence of an inert organic diluent, and if appropriate in the presence of a catalyst.

The formula (XI) provides a general definition of the 2-halogenoaniline derivatives required as reaction components for carrying out the process (g) according to the invention. In this formula, X and m each preferably have those meanings which have already been mentioned in connection with the description of the substances of the formula (I) according to the invention as being preferred or as being particularly preferred for these radicals or these indices. Hal preferably represents fluorine, chlorine or bromine, in particular chlorine or bromine.

The 2-halogenoaniline derivatives of the formula (XI) are commercially available or can be prepared from the corresponding nitro compounds by reduction.

The formula (XII) provides a general definition of the anilineboronic acids required as reaction components for carrying out the process (h) according to the invention. In this formula, X and m each preferably have those meanings which have already been mentioned in connection with the description of the substances of the formula (I) according to the invention as being preferred or as being particularly preferred for these radicals or these indices. $G^1$ and $G^2$ preferably each represent hydrogen or together represent tetramethylethylene.

The anilineboronic acids of the formula (XII) are commercially available.

The formula (IV) provides a general definition of the carboxamide derivatives required as starting materials for carrying out the processes (b) and (f) according to the invention. In this formula, A, X and m each preferably have those meanings which have already been mentioned in connection with the description of the substances of the formula (I) according to the invention as being preferred or as being particularly preferred for these radicals.

The carboxamide derivatives of the formula (IV) are known or can be prepared by known processes (cf. WO 91/01311, EP-A 0 371 950).

The formula (V) provides a general definition of the boronic acid derivatives required for preparing the reaction components when carrying out process (b) and process (g) according to the invention. In this formula, R, Z, Y and n each preferably have those meanings which have already been mentioned in connection with the description of the substances of the formula (I) according to the invention as being preferred or as being particularly preferred for these radicals or these indices. $G^1$ and $G^2$ preferably each represent hydrogen or together represent tetramethylethylene.

The boronic acid derivatives of the formula (V) are novel and can be prepared by i) reacting phenylboronic acids of the formula (XIII)

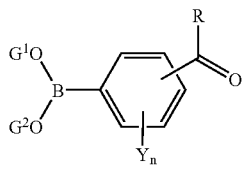

(XIII)

in which

R, Y, n, $G^1$ and $G^2$ are each as defined above, with alkoxamines of the formula (IX)

Z-O—$NH_2$ x HCl    (IX)

in which

Z is as defined above, if appropriate in the presence of an acid binder, and if appropriate in the presence of an inert organic diluent, and if appropriate in the presence of a catalyst.

The formula (XIII) provides a general definition of the phenylboronic acids required as reaction components for carrying out the process (i) according to the invention. In this formula, R, Y and n each preferably have those meanings which have already been mentioned in connection with the description of the substances of the formula (I) according to the invention as being preferred or as being particularly preferred for these radicals or these indices. $G^1$ and $G^2$ preferably each represent hydrogen or together represent tetramethylethylene.

The phenylboronic acids of the formula (XIII) are commercially available.

The formula (VI) provides a general definition of the carboxamide-boronic acid derivatives required as reaction components for carrying out the process (c) according to the invention. In this formula, A, X and m each preferably have those meanings which have already been mentioned in connection with the description of the substances of the formula (I) according to the invention as being preferred or as being particularly preferred for these radicals. $G^1$ and $G^2$ preferably each represent hydrogen or together represent tetramethylethylene.

The carboxamide-boronic acid derivatives of the formula (VI) are novel. They can be prepared by j) reacting carboxylic acid derivatives of the formula (II)

(II)

in which

A and G are each as defined above, with anilineboronic acids of the formula (XII)

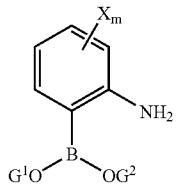

(XII)

in which

X, m, $G^1$ and $G^2$ are each as defined above, if appropriate in the presence of an acid binder, and if appropriate in the presence of an inert organic diluent, and if appropriate in the presence of a catalyst.

The formula (VII) provides a general definition of the phenyloxime derivatives required as reaction components for carrying out the processes (c) and (f) according to the invention and the process (h). In this formula, R, Z, Y and n each preferably have those meanings which have already been mentioned in connection with the description of the substances of the formula (I) according to the invention as being preferred or as being particularly preferred for these radicals.

The phenyloxime derivatives of the formula (VII) are known or can be prepared by known processes (cf. Synth. Commun. 2000, 30, 665–669, Synth. Commun. 1999, 29, 1697–1701).

The formula (VIII) provides a general definition of the biphenylacyl derivatives required as starting materials for carrying out the process (d) according to the invention. In this formula, A, R, X, Y, m and n each have those meanings which have already been mentioned in connection with the description of the substances of the formula (I) according to the invention as being preferred or as being particularly preferred for these radicals.

The biphenylacyl derivatives of the formula (VIII) are novel. They can be prepared by k) reacting carboxylic acid derivatives of the formula (II)

(II)

in which

A and G are each as defined above, with 2-benzaldehyde-aniline derivatives of the formula (XIV)

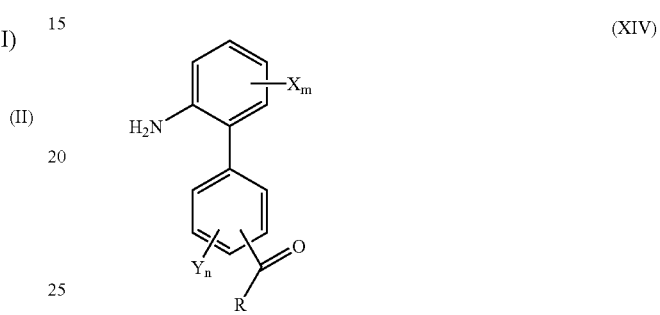

(XIV)

in which

R, X, Y, m and n are each as defined above, if appropriate in the presence of an acid binder, and if appropriate in the presence of an inert organic diluent.

The formula (XIV) provides a general definition of the 2-benzaldehyde-aniline derivatives required as reaction components for carrying out the process (k) according to the invention. In this formula, R, X, Y, m and n each preferably have those meanings which have already been mentioned in connection with the description of the substances of the formula (I) according to the invention as being preferred or as being particularly preferred for these radicals.

The 2-benzaldehyde-aniline derivatives of the formula (XIV) are novel. They can be prepared by l) reacting aniline derivatives of the formula (XI)

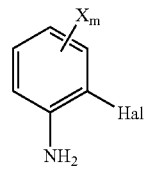

(XI)

in which

X and m are each as defined above and

Hal represents halogen with phenylboronic acid derivatives of the formula (XIII)

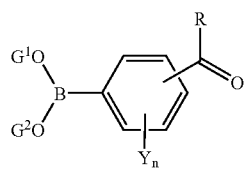

(XIII)

in which

R, Y, n, $G^1$ and $G^2$ are each as defined above, if appropriate in the presence of an acid binder, and if appropriate in the presence of an inert organic diluent.

The aniline derivatives of the formula (XI) required as reaction components for carrying out the process (l) have already been described in the description of process (g).

The phenylboronic acid derivatives of the formula (XIII) required as reaction components for carrying out the process (1) have already been described in the description of process (i).

The formula (IX) provides a general definition of the alkoxamines required as reaction components for carrying out the process (d) according to the invention and the process (i). In this formula, Z preferably has those meanings which have already been mentioned in connection with the description of the substances of the formula (I) according to the invention as being preferred or as being particularly preferred for this radical. Preference is given to using the hydrochlorides mentioned in the description. However, it is also possible to use the free alkoxamines in the process according to the invention.

The alkoxamines of the formula (IX) are commercially available.

The formula (I-a) provides a general definition of the hydroxyamine derivatives required as starting materials for carrying out the process (e) according to the invention. In this formula, A, R, X, Y, m and n each preferably have those meanings which have already been mentioned in connection with the description of the substances of the formula (I) according to the invention as being preferred or as being particularly preferred for these radicals.

The hydroxyamine derivatives of the formula (I-a) according to the invention can be prepared by one of the processes (a), (b), (c), (d) or (f) according to the invention described above.

The formula (X) provides a general definition of the compounds required as reaction components for carrying out the process (e) according to the invention. In this formula, $Z^1$ preferably represents $C_1$–$C_4$-alkyl, particularly preferably methyl or ethyl. E preferably represents chlorine, bromine, iodine, methanesulphonyl or p-toluene-sulphonyl. E particularly preferably represents chlorine or bromine.

The compounds of the formula (X) are commercially available.

Suitable acid binders for carrying out the processes (a), (b), (c), (d), (e) and (f) according to the invention are in each case all inorganic and organic bases which are customary for such reactions. Preference is given to using alkaline earth metal or alkali metal hydroxides, such as sodium hydroxide, calcium hydroxide, potassium hydroxide, or else ammonium hydroxide, alkali metal carbonates, such as sodium carbonate, potassium carbonate, potassium bicarbonate, sodium bicarbonate, alkali metal or alkaline earth metal acetates, such as sodium acetate, potassium acetate, calcium acetate, and also tertiary amines, such as trimethylamine, triethylamine, tributylamine, N,N-dimethylaniline, pyridine, N-methylpiperidine, N,N-dimethylaminopyridine, diazabicyclooctane (DABCO), diazabicyclononene (DBN) or diazabicycloundecene (DBU). However, it is also possible to work in the absence of an additional acid binder or to employ an excess of the amine component, so that it simultaneously acts as acid binder.

Suitable diluents for carrying out the processes (a), (b), (c), (d), (e) and (f) according to the invention are in each case all customary inert organic solvents. Preference is given to using optionally halogenated aliphatic, alicyclic or aromatic hydrocarbons, such as petroleum ether, hexane, heptane, cyclohexane, methylcyclohexane, benzene, toluene, xylene or decalin; chlorobenzene, dichlorobenzene, dichloromethane, chloroform, carbon tetrachloride, dichlorethane or trichlorethane; ethers, such as diethyl ether, diisopropyl ether, methyl t-butyl ether, methyl t-amyl ether, dioxane, tetrahydrofuran, 1,2-dimethoxyethane, 1,2-diethoxyethane or anisole; nitrites, such as acetonitrile, propionitrile, n- or i-butyronitrile or benzonitrile; amides, such as N,N-dimethylformamide, N,N-dimethylacetamide, N-methylformanilide, N-methylpyrrolidone or hexamethylphosphoric triamide; esters, such as methyl acetate or ethyl acetate, sulphoxides, such as dimethyl sulphoxide, or sulphones, such as sulpholane.

When carrying out the processes (a), (b), (c), (d), (e) and (f) according to the invention, the reaction temperatures can in each case be varied within a relatively wide range. In general, the processes are carried out at temperatures between 0° C. and 140° C., preferably between 10° C. and 120° C.

The processes (a), (b), (c), (d), (e) and (f) according to the invention are generally in each case carried out under atmospheric pressure. However, in each case, it is also possible to operate under elevated or reduced pressure.

When carrying out the process (a) according to the invention, in general 1 mol or else an excess of the aniline derivative of the formula (III) and from 1 to 3 mol of acid binder are employed per mole of acid halide of the formula (II). However, it is also possible to employ the reaction components in other ratios. Work-up is carried out by customary methods. In general, the reaction mixture is treated with water and the organic phase is separated off and, after drying, concentrated under reduced pressure. The residue that remains can, if appropriate, be freed by customary methods, such as chromatography or recrystallization, from any impurities that may still be present.

When carrying out the process (b) according to the invention,. in general 1 mol or else an excess of the boronic acid derivative of the formula (V) and from 1 to 5 mol of acid binder are employed per mole of carboxamide of the formula (IV). However, it is also possible to employ the reaction components in other ratios. Work-up is carried out by customary methods. In general, the reaction mixture is treated with water and the precipitate is separated off and dried. The residue that remains can, if appropriate, be freed by customary methods, such as chromatography or recrystallization, from any impurities that may still be present.

When carrying out the process (c) according to the invention, in general 1 mol or else an excess of the phenyloxime derivative of the formula (VII) and from 1 to 10 mol of acid binder and from 0.5 to 5 mol percent of a catalyst are employed per mole of carboxamide-boronic acid derivative of the formula (VI). However, it is also possible to employ the reaction components in other ratios. Work-up is carried out by customary methods. In general, the reaction mixture is treated with water and the precipitate is separated off and dried. The residue that remains can, if appropriate, be freed by customary methods, such as chromatography or recrystallization, from any impurities that may still be present.

When carrying out the process (d) according to the invention, in general 1 mol or else an excess of the alkoxamine of the formula (IX) and from 1 to 5 mol of acid binder are employed per mole of biphenylacyl derivative of the formula (VIII). However, it is also possible to employ the reaction components in other ratios. Work-up is carried out by customary methods. In general, the reaction mixture is treated with water and the precipitate is separated off, washed with water and diisopropyl ether and then dried. The residue that remains can, if appropriate, be freed by customary methods, such as chromatography or recrystallization, from any impurities that may still be present.

When carrying out the process (e) according to the invention, in general 1 mol or else an excess of the reagent of the formula (X) and from 1 to 5 mol of acid binder are employed per mole of hydroxyamine derivative of the formula (I-a). However, it is also possible to employ the reaction components in other ratios. Work-up is carried out by customary methods. In general, the reaction mixture is treated with water and the precipitate is separated off and dried. The residue that remains can, if appropriate, be freed by customary methods, such as chromatography or recrystallization, from any impurities that may still be present.

When carrying out the process (f) according to the invention, in general 1 mol or else an excess of the phenyloxime derivative of the formula (VII) and from 1 to 5 mol of acid binder and 1 to 5 mol of a catalyst are employed per mole of carboxamide derivative of the formula (IV). However, it is also possible to employ the reaction components in other ratios. Work-up is carried out by customary methods. In general, the reaction mixture is treated with water and the precipitate is separated off and dried. The residue that remains can, if appropriate, be freed by customary methods, such as chromatography or recrystallization, from any impurities that may still be present.

The substances according to the invention have potent microbicidal activity and can be employed for controlling undesirable microorganisms, such as fungi and bacteria, in crop protection and in the protection of materials.

Fungicides can be employed in crop protection for controlling Plasmodiophoromycetes, Oomycetes, Chytridiomycetes, Zygomycetes, Ascomycetes, Basidiomycetes and Deuteromycetes.

Bactericides can be employed in crop protection for controlling Pseudomonadaceae, Rhizobiaceae, Enterobacteriaceae, Corynebacteriaceae and Streptomycetaceae.

Some pathogens causing fungal and bacterial diseases which come under the generic names listed above may be mentioned as examples, but not by way of limitation:

Xanthomonas species, such as, for example, *Xanthomonas campestris* pv. *oryzae;*
Pseudomonas species, such as, for example, *Pseudomonas syringae* pv. *lachrymans;*
Erwinia species, such as, for example, *Erwinia amylovora;*
Pythium species, such as, for example, *Pythium ultimum;*
Phytophthora species, such as, for example, *Phytophthora infestans;*
Pseudoperonospora species, such as, for example, *Pseudoperonospora humuli* or *Pseudoperonospora cubensis;*
Plasmopara species, such as, for example, *Plasmopara viticola;*
Bremia species, such as, for example, *Bremia lactucae;*
Peronospora species, such as, for example, *Peronospora pisi* or *P. brassicae;*
Erysiphe species, such as, for example, *Erysiphe graminis;*
Sphaerotheca species, such as, for example, *Sphaerotheca fuliginea;*
Podosphaera species, such as, for example, *Podosphaera leucotricha;*
Venturia species, such as, for example, *Venturia inaequalis;*
Pyrenophora species, such as, for example, *Pyrenophora teres* or *P. graminea* (conidial form: *Drechslera*, syn: *Helminthosporium*);
Cochliobolus species, such as, for example, *Cochliobolus sativus* (conidial form: *Drechslera*, syn: *Helminthosporium*);
Uromyces species, such as, for example, *Uromyces appendiculatus;*
Puccinia species, such as, for example, *Puccinia recondita;*
Sclerotinia species, such as, for example, *Sclerotinia sclerotiorum;*
Tilletia species, such as, for example, *Tilletia caries;*
Ustilago species, such as, for example, *Ustilago nuda* or *Ustilago avenae;*
Pellicularia species, such as, for example, *Pellicularia sasakii;*
Pyricularia species, such as, for example, *Pyricularia oryzae;*
Fusarium species, such as, for example, *Fusarium culmorum;*
Botrytis species, such as, for example, *Botrytis cinerea;*
Septoria species, such as, for example, *Septoria nodorum;*
Leptosphaeria species, such as, for example, *Leptosphaeria nodorum;*
Cercospora species, such as, for example, *Cercospora canescens;*
Alternaria species, such as, for example, *Alternaria brassicae;* and
Pseudocercosporella species, such as, for example, *Pseudocercosporella herpotrichoides.*

The fact that the active compounds are well tolerated by plants at the concentrations required for controlling plant diseases permits the treatment of above-ground parts of plants, of propagation stock and seeds, and of the soil.

The active compounds according to the invention can be employed particularly successfully for controlling diseases in viticulture and fruit and vegetable growing such as, for example, against *Venturia*, *Botrytis*, *Sclerotinia*, *Rhizoctonia*, *Uncinula*, *Sphaerotheca*, *Podosphaera*, *Alternaria* and *Colletotrichum* species. Rice diseases, such as *Pyricularia* and *Pellicularia* species, are likewise controlled with good results.

The active compounds according to the invention are also suitable for increasing the yield of crops. In addition, they show reduced toxicity and are well tolerated by plants.

According to the invention, it is possible to treat all plants and parts of plants. By plants are understood here all plants and plant populations such as desired and undesired wild plants or crop plants (including naturally occurring crop plants). Crop plants can be plants which can be obtained by conventional breeding and optimization methods or by biotechnological and genetic engineering methods or combinations of these methods, including the transgenic plants and including the plant varieties which can or cannot be protected by varietal property rights. Parts of plants are to be understood as meaning all above-ground and below-ground parts and organs of plants, such as shoot, leaf, flower and root, examples which may be mentioned by way of example being leaves, needles, stems, trunks, flowers, fruit bodies, fruits and seeds and also roots, tubers and rhizomes. Parts of plants also include harvested plants and vegetative and generative propagation material, for example seedlings, tubers, rhizomes, cuttings and seeds.

In the protection of materials, the compounds according to the invention can be employed for protecting industrial materials against attack, and destruction by undesired microorganisms.

Industrial materials in the present context are understood as meaning non-living materials which have been prepared for use in industry. For example, industrial materials which are intended to be protected by active compounds according to the invention from microbial change or destruction can be adhesives, sizes, paper and board, textiles, leather, wood, paints and plastic articles, cooling lubricants and other materials which can be attacked, or destroyed by, microorganisms. Parts of production plants, for example cooling-water circuits, which may be impaired by the proliferation of microorganisms may also be mentioned within the scope of the materials to be protected. Industrial materials which may be mentioned within the scope of the present invention are preferably adhesives, sizes, paper and board, leather, wood, paints, cooling lubricants and heat-transfer liquids particularly preferably wood.

Microorganisms capable of degrading or changing industrial materials which may be mentioned are, for example, bacteria, fungi, yeasts, algae and slime organisms. The active compounds according to the invention preferably act against fungi, in particular moulds and wood-discolouring and wood-destroying fungi (Basidiomycetes), and against slime organisms and algae.

Microorganisms of the following genera may be mentioned as examples:
Alternaria, such as Alternaria tenuis,
Aspergillus, such as Aspergillus niger,
Chaetomium, such as Chaetomium globosum,
Coniophora, such as Coniophora puetana,
Lentinus, such as Lentinus tigrinus,
Penicillium, such as Penicillium glaucum,
Polyporus, such as Polyporus versicolor,
Aureobasidium, such as Aureobasidium pullulans,
Sclerophoma, such as Sclerophoma pityophila,
Trichoderma, such as Trichoderma viride,
Escherichia, such as Escherichia coli,
Pseudomonas, such as Pseudomonas aeruginosa, and
Staphylococcus, such as Staphylococcus aureus.

Depending on their particular physical and/or chemical properties, the active compounds can be converted into the customary formulations, such as solutions, emulsions, suspensions, powders, foams, pastes, granules, aerosols and microencapsulations in polymeric substances and in coating compositions for seeds, and ULV cool and warm fogging formulations.

These formulations are produced in a known manner, for example by mixing the active compounds with extenders, that is, liquid solvents, liquefied gases under pressure, and/or solid carriers, optionally with the use of surfactants, that is emulsifiers and/or dispersants, and/or foam formers. If the extender used is water, it is also possible to employ, for example, organic solvents as auxiliary solvents. Essentially, suitable liquid solvents are: aromatics such as xylene, toluene or alkylnaphthalenes, chlorinated aromatics or chlorinated aliphatic hydrocarbons such as chlorobenzenes, chloroethylenes or methylene chloride, aliphatic hydrocarbons such as cyclohexane or paraffins, for example petroleum fractions, alcohols such as butanol or glycol and their ethers and esters, ketones such as acetone, methyl ethyl ketone, methyl isobutyl ketone or cyclohexanone, strongly polar solvents such as dimethylformamide or dimethyl sulphoxide, or else water. Liquefied gaseous extenders or carriers are to be understood as meaning liquids which are gaseous at standard temperature and under atmospheric pressure, for example aerosol propellants such as halogenated hydrocarbons, or else butane, propane, nitrogen and carbon dioxide. Suitable solid carriers are: for example ground natural minerals such as kaolins, clays, talc, chalk, quartz, attapulgite, montmorillonite or diatomaceous earth, and ground synthetic minerals such as finely divided silica, alumina and silicates. Suitable solid carriers for granules are: for example crushed and fractionated natural rocks such as calcite, marble, pumice, sepiolite and dolomite, or else synthetic granules of inorganic and organic meals, and granules of organic material such as sawdust, coconut shells, maize cobs and tobacco stalks. Suitable emulsifiers and/or foam formers are: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates, or else protein hydrolysates. Suitable dispersants are: for example lignin-sulphite waste liquors and methylcellulose.

Tackifiers such as carboxymethylcellulose and natural and synthetic polymers in the form of powders, granules or latices, such as gum arabic, polyvinyl alcohol and polyvinyl acetate, or else natural phospholipids such as cephalins and lecithins and synthetic phospholipids can be used in the formulations. Other possible additives can be mineral and vegetable oils.

It is possible to use colorants such as inorganic pigments, for example iron oxide, titanium oxide and Prussian Blue, and organic dyestuffs such as alizarin dyestuffs, azo dyestuffs and metal phthalocyanine dyestuffs, and trace nutrients such as salts of iron, manganese, boron, copper, cobalt, molybdenum and zinc.

The formulations generally comprise between 0.1 and 95 per cent by weight of active compound, preferably between 0.5 and 90%.

The active compounds according to the invention can be used as such or in their formulations, also in a mixture with known fungicides, bactericides, acaricides, nematicides or insecticides, to broaden, for example, the activity spectrum or to prevent development of resistance. In many cases, synergistic effects are obtained, i.e. the activity of the mixture is greater than the activity of the individual components.

Examples of suitable mixing partners are the following:
Fungicides:
aldimorph, ampropylfos, ampropylfos potassium, andoprim, anilazine, azaconazole, azoxystrobin, benalaxyl, benodanil, benomyl, benzamacril, benzamacril-isobutyl, bialaphos, binapacryl, biphenyl, bitertanol, blasticidin-S, bromuconazole, bupirimate, buthiobate, calcium polysulphide, capsimycin, captafol, captan, carbendazim, carboxin, carvon, quinomethionate, chlobenthiazone, chlorfenazole, chloroneb, chloropicrin, chlorothalonil, chlozolinate, clozylacon, cufraneb, cymoxanil, cyproconazole, cyprodinil, cyprofuram, debacarb, dichlorophen, diclobutrazole, diclofluanid, diclomezine, dicloran, diethofencarb, difenoconazole, dimethirimol, dimethomorph, diniconazole, diniconazole-M, dinocap, diphenylamnine, dipyrithione, ditalimfos, dithianon, dodemorph, dodine, drazoxolon, edifenphos, epoxiconazole, etaconazole, ethirimol, etridiazole, famoxadon, fenapanil, fenarimol, fenbuconazole, fenfuram, fenitropan, fenpiclonil, fenpropidin, fenpropimorph, fentin acetate, fentin hydroxide, ferbam, ferimzone, fluazinam, flumetover, fluoromide, fluquinconazole, flurprimidol, flusilazole, flusulphamide, flutolanil, flutriafol, folpet, fosetyl-aluminium, fosetyl-sodium, fthalide, ffberidazole, furalaxyl, furametpyr, furcarbonil, furconazole, furconazole-cis, furmecyclox, guazatine,
hexachlorobenzene, hexaconazole, hymexazole,
imazalil, imibenconazole, iminoctadine, iminoctadine albesilate, iminoctadine triacetate, iodocarb, ipconazole, iprobenfos (IBP), iprodione, irumamycin, isoprothiolane, isovaledione,
kasugamycin, kresoxim-methyl, copper preparations, such as: copper hydroxide, copper naphthenate, copper oxychloride, copper sulphate, copper oxide, oxine-copper and Bordeaux mixture,
mancopper, mancozeb, maneb, meferimzone, mepanipyrim, mepronil, metalaxyl, metconazole, methasulphocarb, methfuroxam, metiram, metomeclam, metsulphovax, mildiomycin, myclobutanil, myclozolin,
nickel dimethyldithiocarbamate, nitrothal-isopropyl, nuarimol,
ofurace, oxadixyl, oxamocarb, oxolinic acid, oxycarboxim, oxyfenthiin,
paclobutrazole, pefurazoate, penconazole, pencycuron, phosdiphen, pimaricin, piperalin, polyoxin, polyoxorim, probenazole, prochloraz, procymidone, propamocarb, propanosine-sodium, propiconazole, propineb, pyrazophos, pyrifenox, pyrimethanil, pyroquilon, pyroxyfur,
quinconazole, quintozene (PCNB), quinoxyfen,
sulphur and sulphur preparations,
tebuconazole, tecloftalam, tecnazene, tetcyclacis, tetraconazole, thiabendazole, thicyofen, thifluzamide, thiophanate-methyl, thiram, tioxymid, tolclofos-methyl, tolylfluanid, triadimefon, triadimenol, triazbutil, triazoxide, trichlamide, tricyclazole, tridemorph, triflumizole, triforine, triticonazole,
uniconazole,
validamycin A, vinclozolin, viniconazole,
zarilamide, zineb, ziram and also
Dagger G, OK-8705, OK-8801,
α-(1,1-dimethylethyl)-β-(2-phenoxyethyl)-1H-1,2,4-triazole-1-ethanol,
α-(2,4-dichlorophenyl)-β-fluoro-β-propyl-1H-1,2,4-triazole-1-ethanol,
α-(2,4-dichlorophenyl)-β-methoxy-α-methyl-1H-1,2,4-triazole-1-ethanol,
α-(5-methyl-1,3-dioxan-5-yl)-β-[[4-(trifluoromethyl)-phenyl]-methylene]-1H-1,2,4-triazole-1-ethanol,
(5RS,6RS)-6-hydroxy-2,2,7,7-tetramethyl-5-(11H-1,2,4-triazol-1-yl)-3-octanone,
(E)-α-(methoxyimino)-N-methyl-2-phenoxy-phenylacetamide,
1-isopropyl {2-methyl-1-[[[1-(4-methylphenyl)-ethyl]-amino]-carbonyl]-propyl}-carbamate,
1-(2,4-dichlorophenyl)-2-(1H-1,2,4-triazol-1-yl)-ethanone O-(phenylmethyl)-oxime,
1-(2-methyl-1-naphthalenyl)-1H-pyrrole-2,5-dione,
1-(3,5-dichlorophenyl)-3-(2-propenyl)-2,5-pyrrolidinedione,
1-[(diiodomethyl)-sulphonyl]-4-methyl-benzene,
1-[[2-(2,4-dichlorophenyl)-1,3-dioxolan-2-yl]-methyl]-1H-imidazole,
1-[[2-(4-chlorophenyl)-3-phenyloxiranyl]-methyl]-1H-1,2,4-triazole,
1-[1-[2-[(2,4-dichlorophenyl)-methoxy]-phenyl]-ethenyl]-1H-imidazole,
1-methyl-5-nonyl-2-(phenylmethyl)-3-pyrrolidinol,
2',6'-dibromo-2-methyl-4'-trifluoromethoxy-4'-trifluoromethyl-1,3-thiazole-5-carboxanilide,
2,2-dichloro-N-[1-(4-chlorophenyl)-ethyl]-1-ethyl-3-methyl-cyclopropanecarboxamide,
2,6-dichloro-5-(methylthio)-4-pyrimidinyl-thiocyanate,
2,6-dichloro-N-(4-trifluoromethylbenzyl)-benzamide,
2,6-dichloro-N-[[4-(trifluoromethyl)-phenyl]-methyl]-benzamide,
2-(2,3,3-triiodo-2-propenyl)-2H-tetrazole,
2-[(1-methylethyl)-sulphonyl]-5-(trichloromethyl)-1,3,4-thiadiazole,
2-[[6-deoxy-4-O-(4-O-methyl-β-D-glycopyranosyl)-α-D-glucopyranosyl]-amino]-4-methoxy-1H-pyrrolo[2,3-d]pyrimidine-5-carbonitrile,
2-aminobutane,
2-bromo-2-(bromomethyl)-pentanedinitrile,
2-chloro-N-(2,3-dihydro-1,1,3-trimethyl-1H-inden-4-yl)-3-pyridinecarboxamide,
2-chloro-N-(2,6-dimethylphenyl)-N-(isothiocyanatomethyl)-acetamide,
2-phenylphenol (OPP),
3,4-dichloro-1-[4-(difluoromethoxy)-phenyl]-1H-pyrrole-2,5-dione,
3,5-dichloro-N-[cyano[(1-methyl-2-propynyl)-oxy]-methyl]-benzamide,
3-(1,1-dimethylpropyl-1-oxo-1H-indene-2-carbonitrile,
3-[2-(4-chlorophenyl)-5-ethoxy-3-isoxazolidinyl]-pyridine,
4-chloro-2-cyano-N,N-dimethyl-5-(4-methylphenyl)-1H-imidazole-1-sulphonamide,
4-methyl-tetrazolo[1,5-a]quinazolin-5(4H)-one,
8-(1,1-dimethylethyl)-N-ethyl-N-propyl-1,4-dioxaspiro[4.5]decane-2-methanamine,
8-hydroxyquinoline sulphate,
9H-xanthene-2-[(phenylamino)-carbonyl]-9-carboxylic hydrazide,
bis-(1-methylethyl)-3-methyl-4-[(3-methylbenzoyl)-oxy]-2,5-thiophenedicarboxylate,
cis-1-(4-chlorophenyl)-2-(1H-1,2,4-triazol-1-yl)-cycloheptanol,
cis-4-[3-[4-(1,1-dimethylpropyl)-phenyl-2-methylpropyl]-2,6-dimethyl-morpholine hydrochloride,
ethyl [(4-chlorophenyl)-azo]-cyanoacetate,
potassium hydrogen carbonate,
methanetetrathiol sodium salt,
methyl 1-(2,3-dihydro-2,2-dimethyl-1H-inden-1-yl)-1H-imidazole-5-carboxylate,
methyl N-(2,6-dimethylphenyl)-N-(5-isoxazolylcarbonyl)-DL-alaninate,
methyl N-(chloroacetyl)-N-(2,6-dimethylphenyl)-DL-alaninate,
N-(2,3-dichloro-4-hydroxyphenyl)-1-methyl-cyclohexanecarboxamide,
N-(2,6-dimethylphenyl)-2-methoxy-N-(tetrahydro-2-oxo-3-furanyl)-acetamide,
N-(2,6-dimethylphenyl)-2-methoxy-N-(tetrahydro-2-oxo-3-thienyl)-acetamide,
N-(2-chloro-4-nitrophenyl)-4-methyl-3-nitro-benzenesulphonamide,
N-(4-cyclohexylphenyl)-1,4,5,6-tetrahydro-2-pyrimidineamine,
N-(4-hexylphenyl)-1,4,5,6-tetrahydro-2-pyrimidineamine,
N-(5-chloro-2-methylphenyl)-2-methoxy-N-(2-oxo-3-oxazolidinyl)-acetamide,
N-(6-methoxy-3-pyridinyl)-cyclopropanccarboxamide,
N-[2,2,2-trichloro-1-[(chloroacetyl)-amino]-ethyl]-benzamide,
N-[3-chloro-4,5-bis-(2-propinyloxy)-phenyl]-N'-methoxy-methanimidamide,
N-formyl-N-hydroxy-DL-alanine sodium salt,
O,O-diethyl [2-(dipropylamino)-2-oxoethyl]-ethylphosphoramidothioate, O-methyl S-phenyl phenylpropylphosphoramidothioate,
S-methyl 1,2,3-benzothiadiazole-7-carbothioate,
spiro[2H]-1-benzopyran-2,1'(3'H)-isobenzofuran]-3'-one, Bactericides:

bronopol, dichlorophen, nitrapyrin, nickel dimethyldithiocarbamate, kasugamycin, octhilinone, furancarboxylic acid, oxytetracycline, probenazole, streptomycin, tecloftalam, copper sulphate and other copper preparations.

Insecticides/acaricides/nematicides:

abamectin, acephate, acetamiprid, acrinathrin, alanycarb, aldicarb, aldoxycarb, alpha-cypermethrin, alphamethrin, amitraz, avermectin, AZ 60541, azadirachtin, azamethiphos, azinphos A, azinphos M, azocyclotin,

*Bacillus popilliae, Bacillus sphaericus, Bacillus subtilis, Bacillus thuringiensis,* baculoviruses, *Beauveria bassiana, Beauveria tenella,* bendiocarb, benfuracarb, bensultap, benzoximate, betacyfluthrin, bifenazate, bifenthrin, bioethanomethrin, biopermethrin, BPMC, bromophos A, bufencarb, buprofezin, butathiofos, butocarboxim, butylpyridaben, cadusafos, carbaryl, carbofuran, carbophenothion, carbosulphan, cartap, chloethocarb, chlorethoxyfos, chlorfenapyr, chlorfenvinphos, chlorfluazuron, chlormephos, chlorpyrifos, chlorpyrifos M, chlovaporthrin, cis-resmethrin, cispermethrin, clocythrin, cloethocarb, clofentezine, cyanophos, cycloprene, cycloprothrin, cyfluthrin, cyhalothrin, cyhexatin, cypernethrin, cyromazine, deltamethrin, demeton M, demeton S, demeton-S-methyl, diafenthiuron, diazinon, dichlorvos, diflubenzuron, dimethoat, dimethylvinphos, diofenolan, disulphoton, docusat-sodium, dofenapyn, elfusilanate, emamectin, empenthrin, endosulphan, *Entomopfthora* spp., esfenvalerate, ethiofencarb, ethion, ethoprophos, etofenprox, etoxazole, etrimfos, fenamiphos, fenazaquin, fenbutatin oxide, fenitrothion, fenothiocarb, fenoxacrim, fenoxycarb, fenpropathrin, fenpyrad, fenpyrithrin, fenpyroximate, fenvalerate, fipronil, fluazinam, fluazuron, flubrocythrinate, flucycloxuron, flucythrinate, flufenoxuron, flutenzine, fluvalinate, fonophos, fosmethilan, fosthiazate, fubfenprox, furathiocarb, granulosis viruses, halofenozide, HCH, heptenophos, hexaflumuron, hexythiazox, hydroprene, imidacloprid, isazofos, isofenphos, isoxathion, ivermectin, nuclear polyhedrosis viruses, lambda-cyhalothrin, lufenuron, malathion, mecarbam, metaldehyde, methamidophos, *Metharhizium anisopliae, Metharhizium flavoviride,* methidathion, methiocarb, methomyl, methoxyfenozide, metolcarb, metoxadiazone, mevinphos, milbemectin, monocrotophos, naled, nitenpyram, nithiazine, novaluron, omethoat, oxamyl, oxydemethon M,

*Paecilomyces fumosoroseus,* parathion A, parathion M, permethrin, phenthoat, phorat, phosalone, phosmet, phosphamidon, phoxim, pirimicarb, pirimiphos A, pirimiphos M, profenofos, promecarb, propoxur, prothiofos, prothoat, pymetrozine, pyraclofos, pyresmethrin, pyrethrum, pyridaben, pyridathion, pyrimidifen, pyriproxyfen, quinalphos, ribavirin, salithion, sebufos, silafluofen, spinosad, sulphotep, sulprofos, tau-fluvalinate, tebufenozide, tebufenpyrad, tebupirimiphos, teflubenzuron, tefluthrin, temephos, temivinphos, terbufos, tetrachlorvinphos, thetacypermethrin, thiamethoxam, thiapronil, thiatriphos, thiocyclam hydrogen oxalate,
thiodicarb, thiofanox, thuringiensin, tralocythrin, tralomethrin, triarathene, triazamate, triazophos, triazuron, trichlophenidine, trichlorfon, triflumuron, trimethacarb, vamidothion, vaniliprole, *Verticillium lecanii,*

YI 5302, zeta-cypermethrin, zolaprofos (1R-cis)-[5-(phenyhnethyl)-3-furanyl]-methyl-3-[(dihydro-2-oxo-3(2H)-furanylidene)-methyl]-2,2-dimethylcyclopropanecarboxylate, (3-phenoxyphenyl)-methyl-2,2,3,3-tetramethylcyclopropanecarboxylate, 1-[(2-chloro-5-thiazolyl)methyl]tetrahydro-3,5-dimethyl-N-nitro-1,3,5-triazine-2(1H)-imine, 2-(2-chloro-6-fluorophenyl)-4-[4-(1,1-dimethylethyl)phenyl]-4,5-dihydro-oxazole, 2-(acetlyoxy)-3-dodecyl-1,4-naphthalenedione, 2-chloro-N-[[[4-(1-phenylethoxy)-phenyl]-amino]-carbonyl]-benzamide, 2-chloro-N-[[[4-(2,2-dichloro-1,1-difluoroethoxy)-phenyl]-amino]-carbonyl]-benzamide, 3-methylphenyl propylcarbamate 4-[4-(4-ethoxyphenyl)-4-methylpentyl]1-fluoro-2-phenoxybenzene, 4-chloro-2-(1,1-dimethylethyl)-5-[[2-(2,6-dimethyl-4-phenoxyphenoxy)ethyl]thio]-3(2H)-pyridazinone, 4-chloro-2-(2-chloro-2-methylpropyl)-5-[(6-iodo-3-pyridinyl)methoxy]-3(2H)-pyridazinone 4-chloro-5-[(6-chloro-3-pyridinyl)methoxy]-2-(3,4-dichlorophenyl)-3(2H)-pyridazinone,

*Bacillus thuringiensis* strain EG-2348,

[2-benzoyl-1-(1,1-dimethylethyl)-hydrazinobenzoic acid, 2,2-dimethyl-3-(2,4-dichlorophenyl)-2-oxo-1-oxaspiro[4.5]dec-3-en-4-yl butanoate,

[3-[(6-chloro-3-pyridinyl)methyl]-2-thiazolidinylidene]-cyanamide, dihydro-2-(nitromethylene)-2H-1,3-thiazine-3(4H)-carboxaldehyde, ethyl [2-[[1,6-dihydro-6-oxo-1-(phenylmethyl)-4-pyridazinyl]oxy]ethyl]-carbamate, N-(3,4,4-trifluoro-1-oxo-3-butenyl)-glycine, N-(4-chlorophenyl)-3-[4-(difluoromethoxy)phenyl]-4,5-dihydro-4-phenyl-1H-pyrazole-1-carboxamide, N-[(2-chloro-5-thiazolyl)methyl]-N'-methyl-N''-nitroguanidine, N-methyl-N'-(1-methyl-2-propenyl)-1,2-hydrazinedicarbothioamide, N-methyl-N'-2-propenyl-1,2-hydrazinedicarbothioamide, O,O-diethyl [2-(dipropylamino)-2-oxoethyl]-ethylphosphoramidothioate.

A mixture with other known active compounds, such as herbicides, or with fertilizers and growth regulators, is also possible.

In addition, the compounds of the formula (I) according to the invention also have very good antimycotic activity. They have a very broad antimycotic activity spectrum in particular against dermatophytes and yeasts, moulds and diphasic fungi, for example against *Candida* species, such as *Candida albicans, Candida glabrata, Epidermophyton* species, such as *Epidermophyton floccosum, Aspergillus* species, such as *Aspergillus niger* and *Aspergillus fumigatus, Trichophyton* species, such as *Trichophyton mentagrophytes, Microsporon* species such as *Microsporon canis* and *audouinii.*

The list of these fungi in no way limits the mycotic spectrum which can be covered, but is only for illustration.

The active compounds can be used as such, in the form of their formulations or the use forms prepared therefrom, such as ready-to-use solutions, suspensions, wettable powders, pastes, soluble powders, dusts and granules. Application is carried out in a customary manner, for example by watering, spraying, atomizing, broadcasting, dusting, foaming, spreading, etc. It is furthermore possible to apply the active compounds by the ultra-low volume method, or to inject the active compound preparation or the active compound itself into the soil. It is also possible to treat the seeds of the plants.

When using the active compounds according to the invention as fungicides, the application rates can be varied within a relatively wide range, depending on the kind of application. For the treatment of parts of plants, the active compound application rates are generally between 0.1 and 10,000 g/ha, preferably between 10 and 1000 g/ha. For seed dressing, the active compound application rates are generally between 0.001 and 50 g per kilogram of seed, preferably between 0.01 and 10 g per kilogram of seed. For the treatment of the soil, the active compound application rates are generally between 0.1 and 10,000 g/ha, preferably between 1 and 5000 g/ha.

The compositions used for protecting industrial materials comprise the active compounds generally in an amount of from 1 to 95%, preferably from 10 to 75%.

The use concentrations of the active compounds according to the invention depend on the nature and occurrence of the microorganisms to be controlled and on the composition of the material to be protected. The optimum amount employed can be determined by a series of tests. In general, the use concentrations are in the range from 0.001 to 5% by weight, preferably from 0.05 to 1.0% by weight, based on the material to be protected.

The activity and the activity spectrum of the active compounds to be used according to the invention in material protection, or the compositions, concentrates or quite generally formulations preparable therefrom can be increased by adding, if appropriate, further antimicrobially active compounds, fungicides, bactericides, herbicides, insecticides or other active compounds for widening the activity spectrum or obtaining particular effects, such as, for example, additional protection against insects. These mixtures may have a wider activity spectrum than the compounds according to the invention.

The preparation and the use of the active compounds according to the invention is shown in the examples below.

PREPARATION EXAMPLES

Example 1

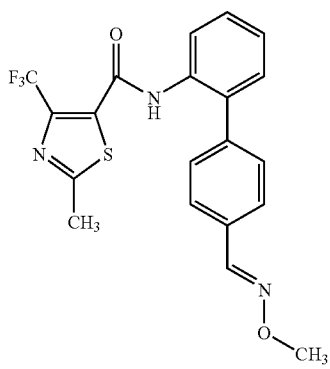

Process (a):

At room temperature, a solution of 0.59 g (0.0026 mol) of 2-(4-methoximinomethylphenyl)-aniline in 25 ml of toluene is treated with 0.26 g (0.0026 mol) of triethylamine. At room temperature, a solution of 0.6 g (0.0026 mol) of 2-methyl-4-trifluoromethylthiazole-5-carbonyl chloride in 5 ml of toluene is allowed to run this mixture while stirring into. After the addition has ended, the reaction mixture is heated to 50° C. and stirred at this temperature for 2 h. For work-up, the reaction mixture is cooled to room temperature and admixed with water. The organic phase is separated off, dried over sodium sulphate, filtered and concentrated under reduced pressure. The residue that remains is chromatographed on silica gel using the mobile phase cyclohexane:ethyl acetate=3:1. The eluate is concentrated, giving 0.81 g (74% of theory) of 2'-(4-methoximinomethyl-phenyl)-2-methyl-4-trifluoromethylthiazole-5-carboxanilide as a solid of melting point 122 to 123° C.

Preparation of Starting Materials

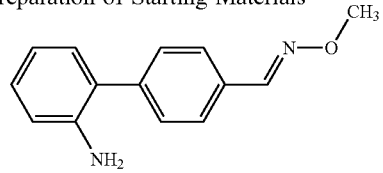

At room temperature, a mixture of 2.9 g (0.017 mol) of 2-bromoaniline, 0.68 g of tetrakis-(triphenylphosphine)palladium, 5.5 g (0.031 mol) of 4-methoximinomethyl-phenylboronic acid and 40 ml of 1,2-dimethoxyethane is treated with a solution of 8.2 g (0.077 mol) of sodium carbonate in 35 ml of water. The reaction mixture is then heated to reflux temperature and boiled for 12 h. For work-up, the mixture is cooled to room temperature and extracted with diethyl ether. The organic phase is separated off and admixed with water. The organic phase is again separated off, dried over sodium sulphate and finally concentrated under reduced pressure. The residue that remains is chromatographed on silica gel using the mobile phase cyclohexane:ethyl acetate=3:1. The eluate is concentrated, giving 3.8 g (98.8% of theory based on 2-bromoaniline) of 2-(4-methoximinomethyl-phenyl)-aniline in the form of an oil. $^1$H-NMR spectrum (DMSO/TMS): δ=3.90 (3H) ppm.

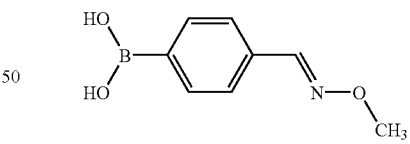

A mixture of 5.0 g (0.033 mol) of 4-formylphenylboronic acid, 3.4 g (0.041 mol) of methoxylamine hydrochloride, 3.4 g (0.041 mol) of sodium acetate, 40 ml of methanol and 10 ml of water is stirred at room temperature for 12 h. For work-up, the reaction mixture is stirred with water and the resulting precipitate is filtered off with suction, washed with water and dried at 50° C. under reduced pressure. This gives 5.56 g (93.1% of theory) of 4-methoximinomethyl-phenylboronic acid as colourless crystals of melting point 199–200° C.

The biphenylcarboxamides of the formula (I) listed in the table below are also prepared by the methods described above.

TABLE 1

(I)

| Ex. No. | | Physical constant |
|---|---|---|
| 2 | | logP 3.42[a] |
| 3 | | logP 4.65[a] |
| 4 | | m.p. 107–109° C. |
| 5 | | logP 4.23[a] |

TABLE 1-continued
(I)
| Ex. No. | | Physical constant |
|---|---|---|
| 6 | 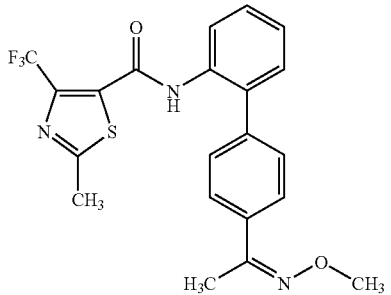 | m.p. 129–131° C. |
| 7 | 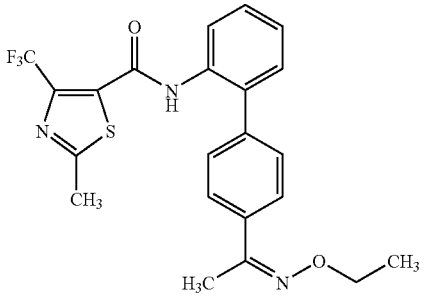 | m.p. 125–128° C. |
| 8 | 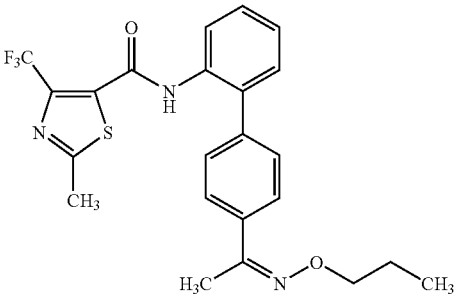 | m.p. 110–112° C. |
| 9 | 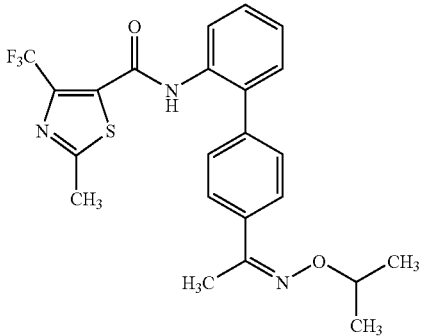 | m.p. 118–120° C. |

TABLE 1-continued
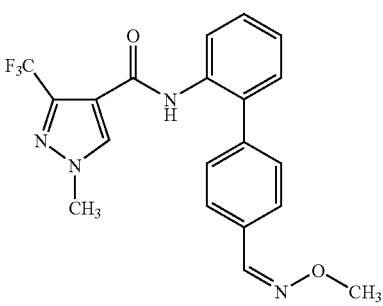
(I)
| Ex. No. | | Physical constant |
|---|---|---|
| 10 | 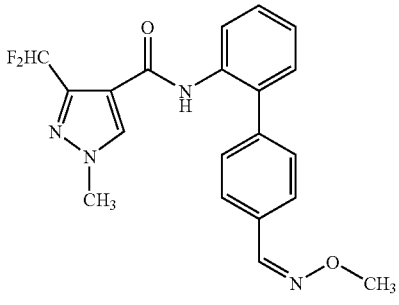 | m.p. 158–160° C. |
| 11 | 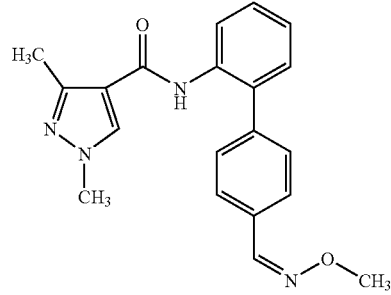 | m.p. 127–129° C. |
| 12 | 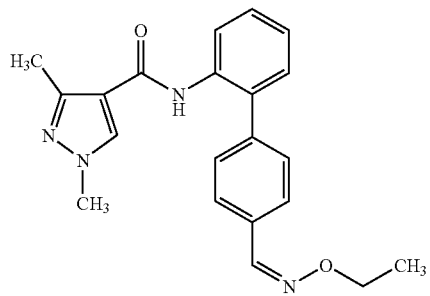 | m.p. 146° C. |
| 13 | | m.p. 137–139° C. |

TABLE 1-continued (I)

| Ex. No. | Physical constant |
|---|---|
| 14 | m.p. 152–153° C. |
| 15 | |
| 16 | |
| 17 | logP 3.24[a] |

TABLE 1-continued
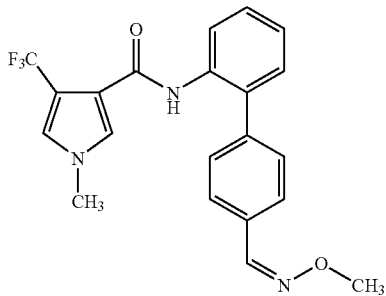
(I)
| Ex. No. | | Physical constant |
|---|---|---|
| 18 | 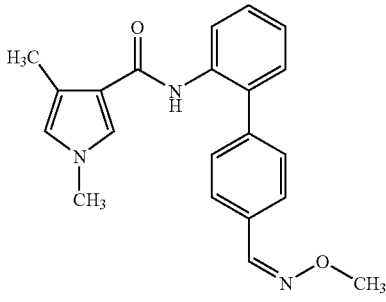 | m.p. 141–143° C. |
| 19 | | logP 5.10[a] |
| 20 | 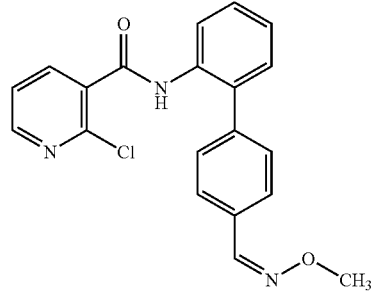 | m.p. 116–119° C. |

TABLE 1-continued
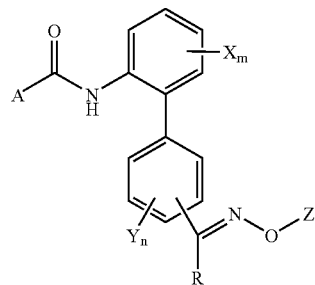
| Ex. No. | | Physical constant |
|---|---|---|
| 21 | | m.p. 144–147° C. |
| 22 | | logP 4.26[(a)] |
| 23 | | logP 4.26[(a)] |

TABLE 1-continued
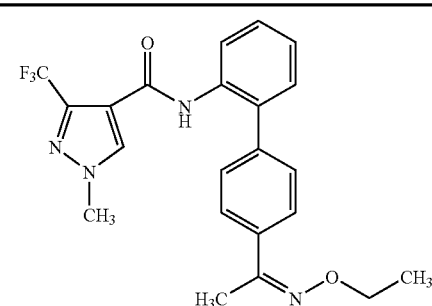
(I)
| Ex. No. | | Physical constant |
|---|---|---|
| 24 | 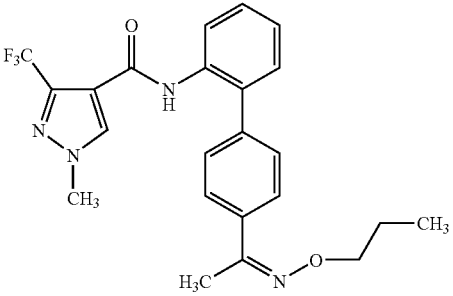 | m.p. 160–162° C. |
| 25 | | m.p. 148–150° C. |
| 26 | 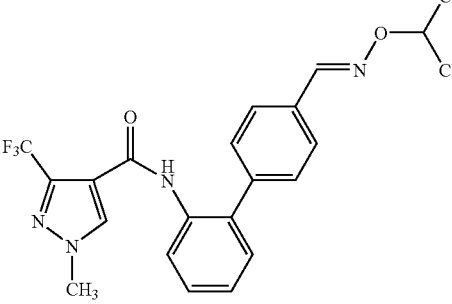 | m.p. 126–128° C. |
| 27 | 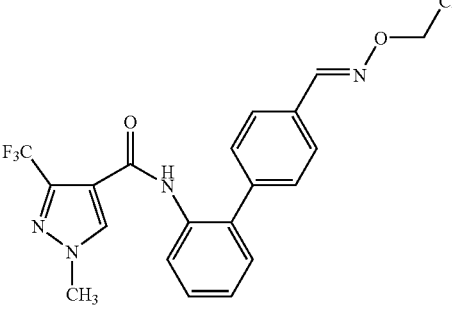 | m.p. 170–172° C. |

TABLE 1-continued
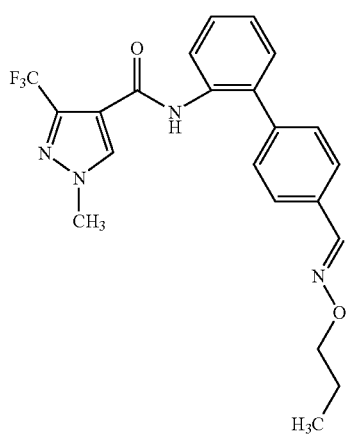
(I)
| Ex. No. | | Physical constant |
|---|---|---|
| 28 | 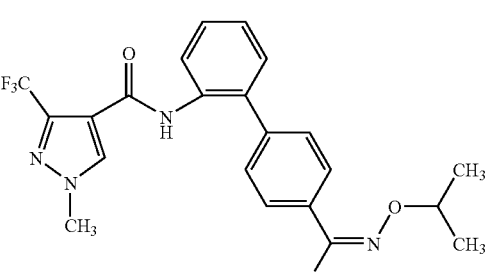 | logP 3.86[a] |
| 29 | | m.p. 164–166° C. |
| 30 | 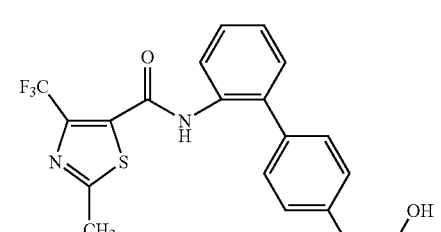 | logP 2.78[a] |
| 31 | 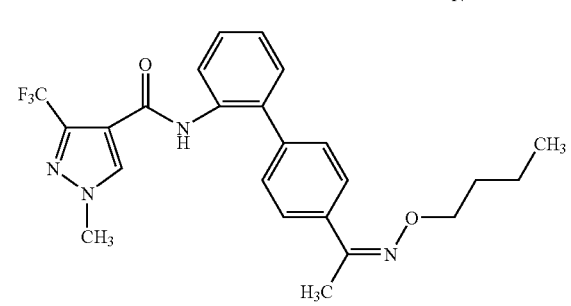 | m.p. 89–91° C. |

TABLE 1-continued
(I)
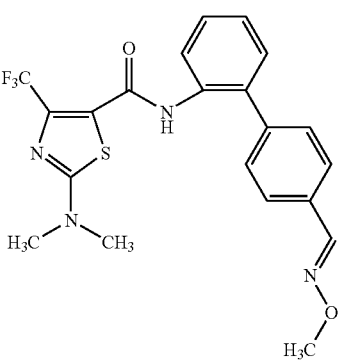
| Ex. No. | | Physical constant |
|---|---|---|
| 32 | 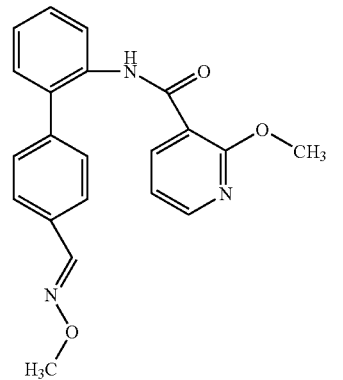 | logP 3.84[a] |
| 33 | | logP 4.12[a] |
| 34 | 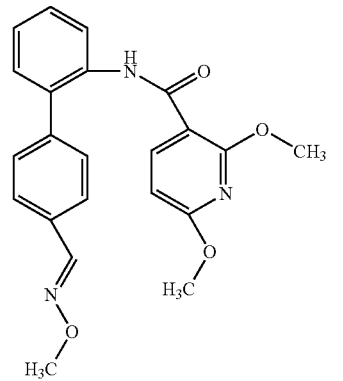 | logP 4.73[a] |

TABLE 1-continued
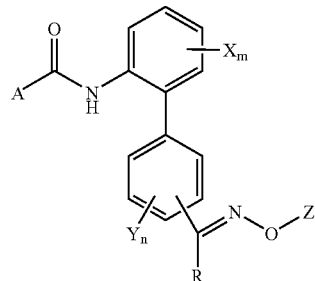
(I)
| Ex. No. | | Physical constant |
|---|---|---|
| 35 | | logP 2.04[a] |
| 36 | | logP 3.75[a] |
| 37 | | logP 4.08[a] |

TABLE 1-continued
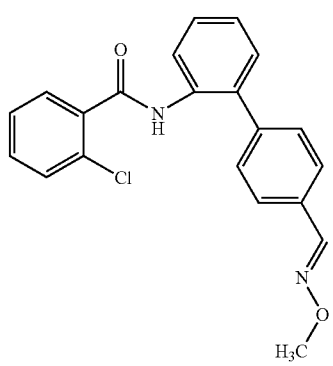
(I)
| Ex. No. | | Physical constant |
|---|---|---|
| 38 | 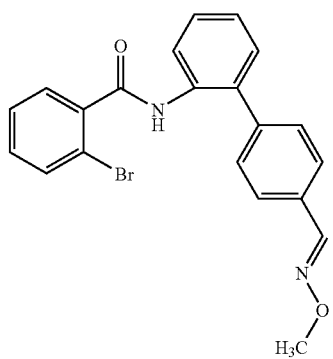 | logP 3.59[a] |
| 39 | | logP 3.61[a] |
| 40 | 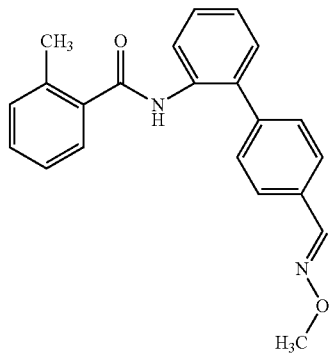 | logP 3.56[a] |

TABLE 1-continued
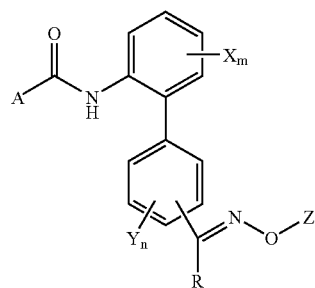
| Ex. No. | | Physical constant |
|---|---|---|
| 41 | | logP 3.19[a] |
| 42 | | logP 3.47[a] |
| 43 | | logP 3.47[a] |
| 44 | | logP 3.76[a] |

TABLE 1-continued
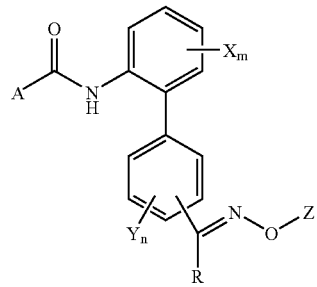
| Ex. No. | | Physical constant |
|---|---|---|
| 45 | | logP 3.73[a] |
| 46 | | logP 3.73[a] |
| 47 | | logP 3.86[a] |
| 48 | | logP 3.84[a] |

TABLE 1-continued
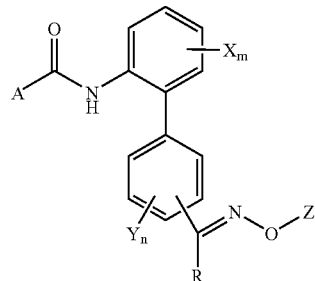
(I)
| Ex. No. | | Physical constant |
|---|---|---|
| 49 | 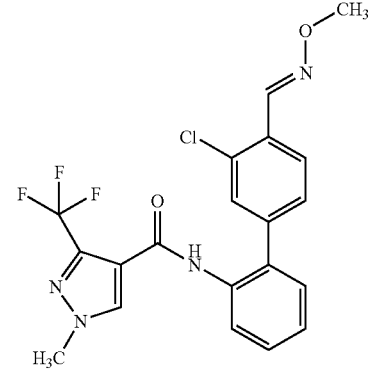 | logP 3.54[a] |
| 50 | 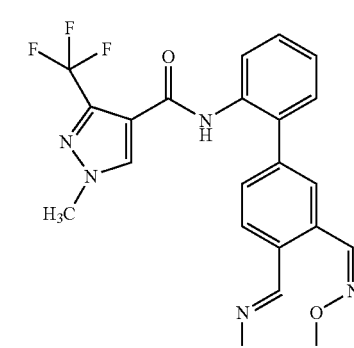 | logP 3.36[a] |
| 51 | 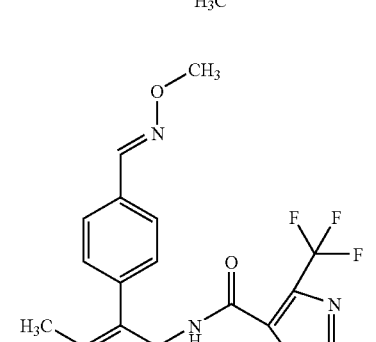 | logP 3.78[a] |

TABLE 1-continued
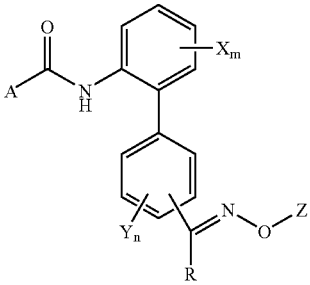
(I)
| Ex. No. | | Physical constant |
|---|---|---|
| 52 | 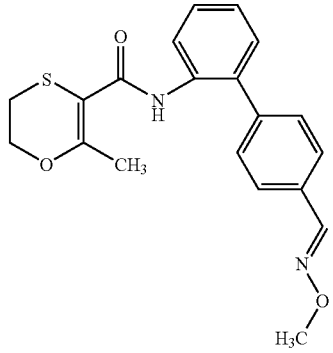 | logP 3.25[a] |
| 53 | | logP 3.75[a] |
| 54 | 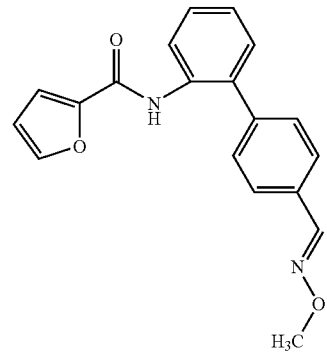 | logP 3.20[a] |
| 55 | 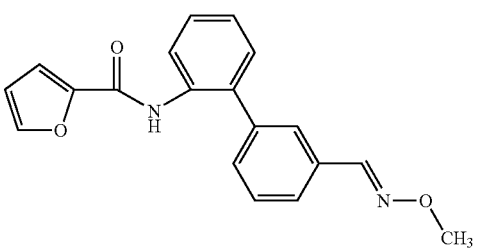 | logP 3.20[a] |

TABLE 1-continued
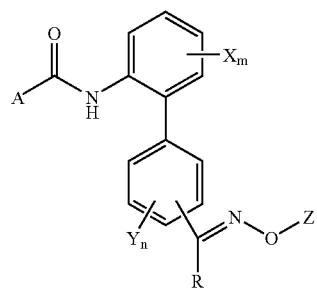
(I)
| Ex. No. | | Physical constant |
|---|---|---|
| 56 | 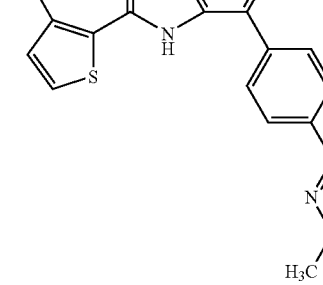 | logP 4.39[a] |
| 57 | 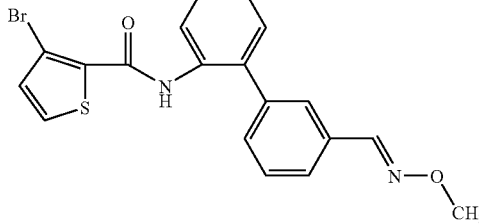 | logP 4.39[a] |
| 58 | 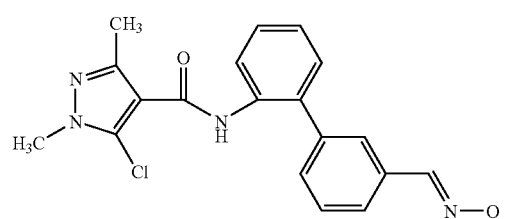 | logP 3.37[a] |
| 59 | 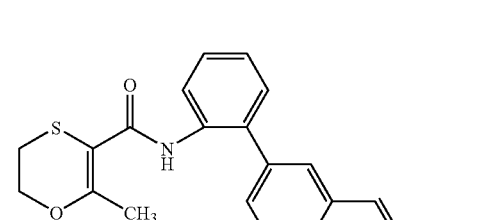 | logP 3.64[a] |

TABLE 1-continued (I)

| Ex. No. | Structure | Physical constant |
|---|---|---|
| 60 | 4-(difluoromethyl)-2-methyl-N-(4'-((E)-(methoxyimino)methyl)-[1,1'-biphenyl]-2-yl)thiazole-5-carboxamide | logP 3.26[a] |
| 61 | 4-(difluoromethyl)-2-methyl-N-(3'-((E)-(methoxyimino)methyl)-[1,1'-biphenyl]-2-yl)thiazole-5-carboxamide | logP 3.26[a] |
| 62 | N-(4'-((E)-(methoxyimino)methyl)-[1,1'-biphenyl]-2-yl)-5-(trifluoromethyl)furan-2-carboxamide | logP 3.99[a] |
| 63 | N-(3'-((E)-(methoxyimino)methyl)-[1,1'-biphenyl]-2-yl)-5-(trifluoromethyl)furan-2-carboxamide | logP 4.02[a] |

TABLE 1-continued
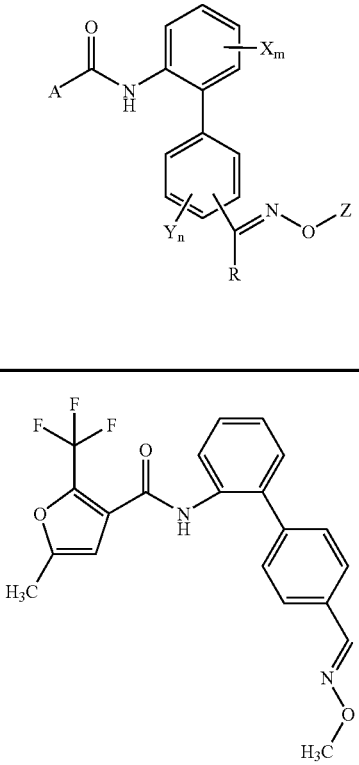
(I)
| Ex. No. | | Physical constant |
|---|---|---|
| 64 | 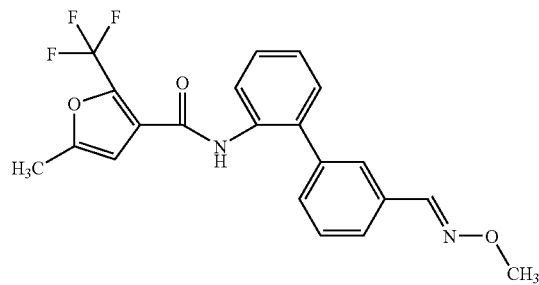 | logP 3.94[a] |
| 65 | | logP 3.97[a] |
| 66 | 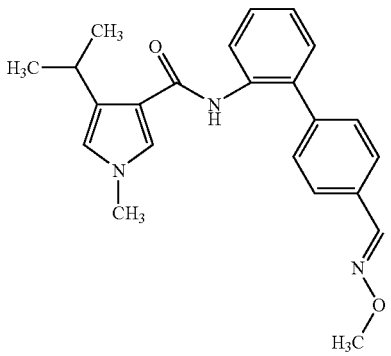 | logP 3.82[a] |

TABLE 1-continued
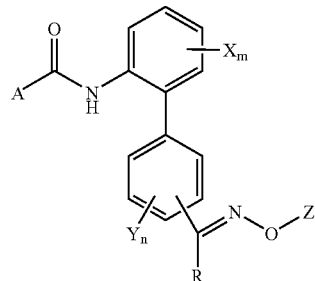
(I)
| Ex. No. | Physical constant |
|---|---|
| 67 | logP 3.75[a] |
| 68 | logP 3.75[a] |
| 69 | logP 4.40[a] |

TABLE 1-continued
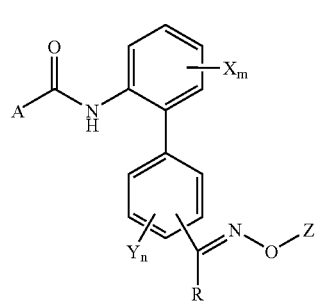
(I)
| Ex. No. | | Physical constant |
|---|---|---|
| 70 | | logP 4.45[a] |
| 71 | | logP 3.78[a] |
| 72 | | logP 3.80[a] |
| 73 | | logP 4.00[a] |

TABLE 1-continued (I)

| Ex. No. | | Physical constant |
|---|---|---|
| 74 | | logP 3.95[a] |
| 75 | | m.p. 129–131° C. |
| 76 | | m.p. 157–158° C. |
| 77 | | logP 4.77[a] |

TABLE 1-continued
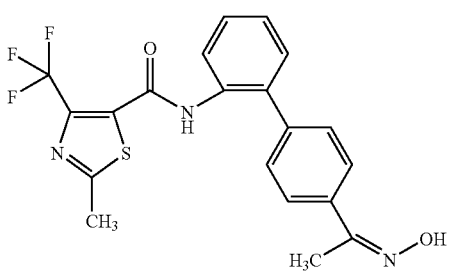
(I)
| Ex. No. | | Physical constant |
|---|---|---|
| 78 | 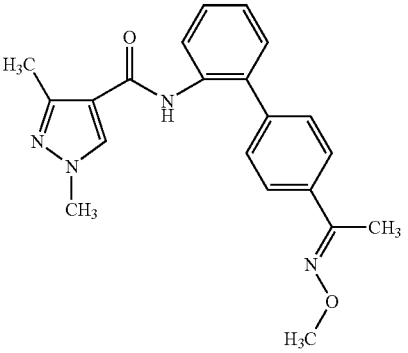 | |
| 79 | | m.p. 107–109° C. |
| 80 | 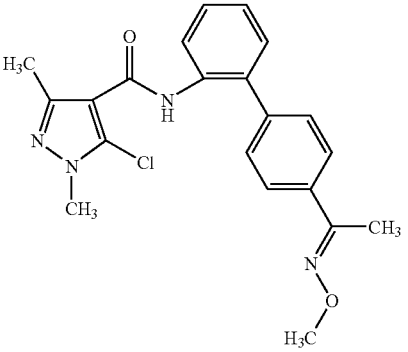 | m.p. 168–171° C. |

TABLE 1-continued (I)

| Ex. No. | | Physical constant |
|---|---|---|
| 81 | | m.p. 148–150° C. |
| 82 | | m.p. 118° C. |
| 83 | | m.p 119–121° C. |

TABLE 1-continued (I)

| Ex. No. | | Physical constant |
|---|---|---|
| 84 | | m.p. 160–162° C. |
| 85 | | |
| 86 | | m.p. 115–117° C. |

TABLE 1-continued
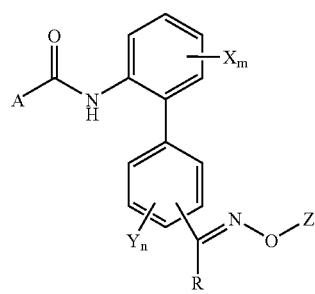
(I)
| Ex. No. | | Physical constant |
|---|---|---|
| 87 | | m.p. 98° C. |
| 88 | | m.p. 108–110° C. |
| 89 | | m.p. 119–121° C. |

TABLE 1-continued
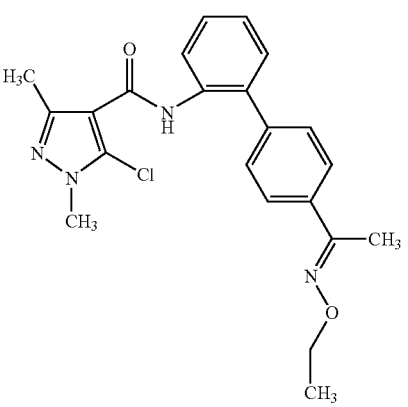
(I)
| Ex. No. | Physical constant |
|---|---|
| 90 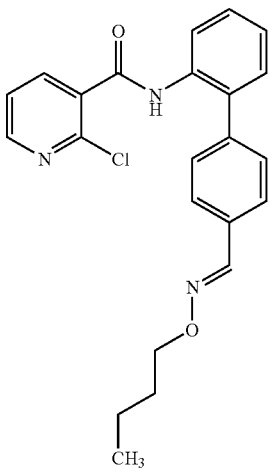 | m.p. 80–82° C. |
| 91 | m.p. 68–70° C. |

TABLE 1-continued (I)

| Ex. No. | | Physical constant |
|---|---|---|
| 92 | | m.p. 55–57° C. |
| 93 | | m.p. 110–112° C. |
| 94 | | |

TABLE 1-continued
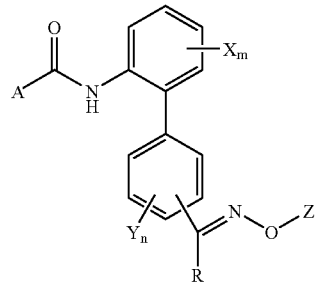
(I)
| Ex. No. | | Physical constant |
|---|---|---|
| 95 | 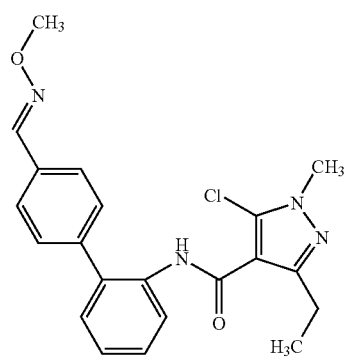 | logP 3.68[a] |
| 96 | 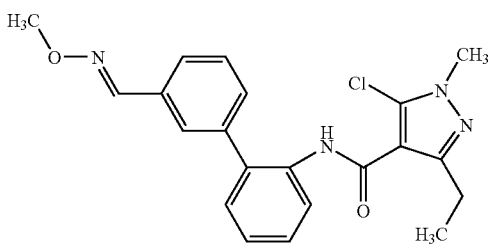 | logP 3.72[a] |
| 97 | 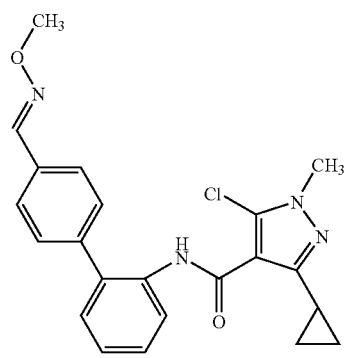 | logP 3.76[a] |
| 98 | 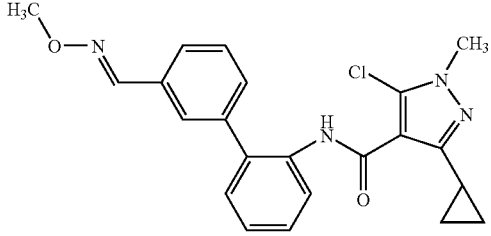 | logP 3.81[a] |

TABLE 1-continued
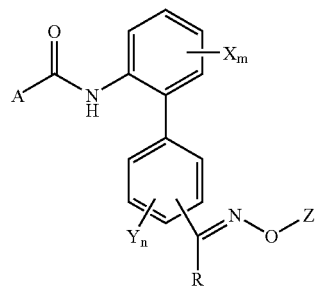
(I)
| Ex. No. | | Physical constant |
|---|---|---|
| 99 | | logP 4.67[(a)] |
| 100 | | logP 4.72[(a)] |
| 101 | | logP 3.26[(a)] |
| 102 | | logP 3.26[(a)] |

TABLE 1-continued (I)

| Ex. No. | | Physical constant |
|---|---|---|
| 103 | | logP 3.87[a] |
| 104 | | m.p. 94–97° C. |
| 105 | | m.p. 103–105° C. |

TABLE 1-continued
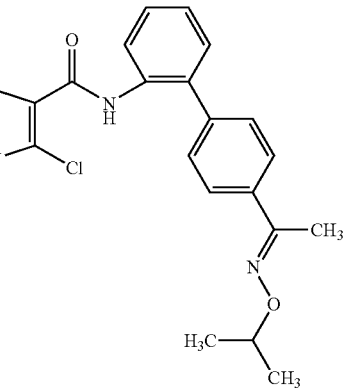
(I)
| Ex. No. | | Physical constant |
|---|---|---|
| 106 | 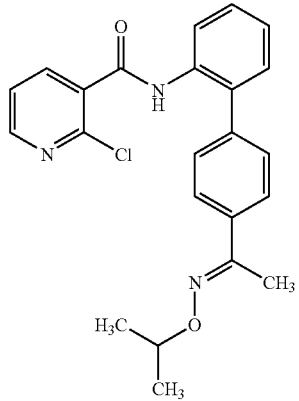 | m.p. 108–109° C. |
| 107 | | m.p. 84–86° C. |
| 108 | 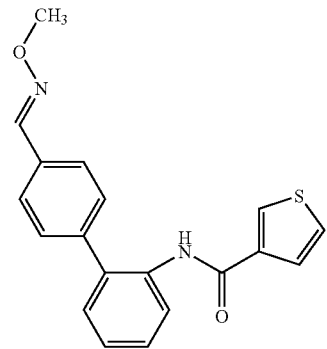 | logP 3.10[(a)] |

TABLE 1-continued
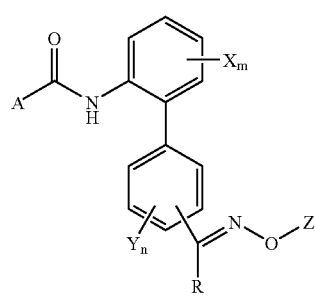
| Ex. No. | | Physical constant |
|---|---|---|
| 109 | | |
| 110 | | logP 3.58[(a)] |
| 111 | | logP 3.59[(a)] |
| 112 | | logP 3.21[(a)] |

TABLE 1-continued
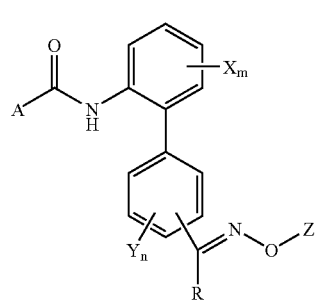
(I)
| Ex. No. | | Physical constant |
|---|---|---|
| 113 | | logP 2.43[(a)] |
| 114 | | logP 3.00[(a)] |
| 115 | | m.p. 157–159° C. |

TABLE 1-continued
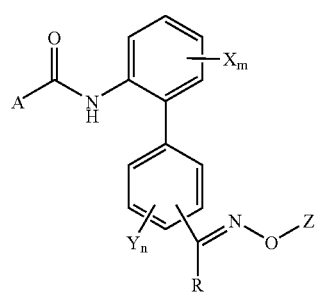
(I)
| Ex. No. | | Physical constant |
|---|---|---|
| 116 | | Fp. 70–72° C. |
| 117 | | Fp. 75° C. |
| 118 | | logP 4.22[(a)] |

TABLE 1-continued
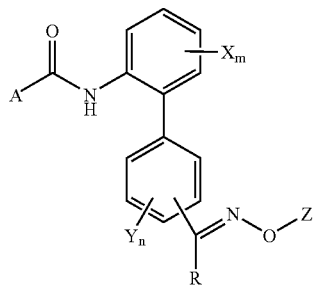
(I)
| Ex. No. | | Physical constant |
|---|---|---|
| 119 | 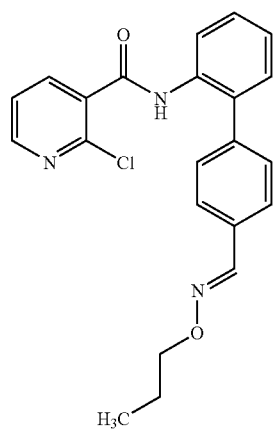 | Fp. 90–92° C. |
| 120 | 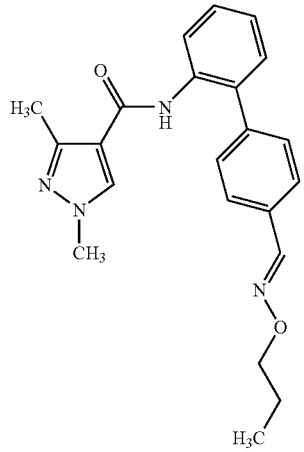 | Fp. 141–143° C. |

TABLE 1-continued

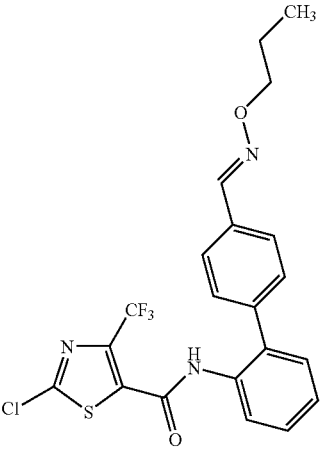

| Ex. No. | | Physical constant |
|---|---|---|
| 121 | | Fp. 82–84° C. |

The logP values given in Table 1 were determined in accordance with EEC Directive 79/831 Annex V.A8 by HPLC (High Performance Liquid Chromotography) on a reversed-phase column (C 18). Temperature: 43° C.

[a] Mobile phases for the determination in the acidic range: 0.1% aqueous phosphoric acid, acetonitrile; linear gradient from 10% acetonitrile to 90% acetonitrile - the corresponding measurement results in Table 1 are marked[a].

[b] Mobile phases for the determination in the neutral range: 0.01 molar aqueous phosphate buffer solution, acetonitrile; linear gradient from 10% acetonitrile to 90% acetonitrile - corresponding measurement results in Table 1 are marked[b].

Calibration was carried out using unbranched alkan-2-ones (having 3 to 16 carbon atoms) with known logP values (determination of the logP values by the retention times using linear interpolation between two successive alkanones).

The lambda max values were determined in the maxima of the chromatographic signals using the UV spectra from 200 nm to 400 mm.

Use Examples

Example A

Podosphaera Test (apple)/Protective

Solvent: 24.5 parts by weight of acetone 24.5 parts by weight of dimethylacetamide
Emulsifier; 1.0 part by weight of alkyl-aryl polyglycol ether To produce a suitable preparation of active compound, 1 part by weight of active compound is mixed with the stated amounts of solvent and emulsifier, and the concentrate is diluted with water to the desired concentration.

To test for protectiv activity, young plants are sprayed with the preparation of active compound at the stated application rate. After the spray coating has dried on, the plants are inoculated with an aqueous spore suspension of the apple mildew pathogen *Podosphaera leucotricha*. The plants are then placed in a greenhouse at approximately 23° C. and a relative atmospheric humidity of approximately 70%.

Evaluation is carried out 10 days after the inoculation. 0% means an efficacy which corresponds to that of the control, whereas an efficacy of 100% means that no infection is observed.

In this test, for example, the following compounds according to the invention of the Preparation Examples exhibit an activity which is superior to that of the prior art:

TABLE A

Podosphaera test (apple) / protective

| Active compound | | Application rate of active compound in g/ha | % Efficacy |
|---|---|---|---|
| (I-1) | [Structure: 2-methyl-4-(trifluoromethyl)thiazole-5-carboxamide linked to biphenyl with =N-OCH₃ oxime] | 100 | 100 |
| (I-3) | [Structure: 2-methyl-4-(trifluoromethyl)thiazole-5-carboxamide linked to biphenyl with =N-O-butyl oxime] | 100 | 100 |
| (I-4) | [Structure: 2-methyl-4-(trifluoromethyl)thiazole-5-carboxamide linked to biphenyl with =N-O-ethyl oxime] | 100 | 95 |
| (I-5) | [Structure: 2-methyl-4-(trifluoromethyl)thiazole-5-carboxamide linked to biphenyl with =N-O-isopropyl oxime] | 100 | 100 |

TABLE A-continued

Podosphaera test (apple) / protective

| Active compound | Application rate of active compound in g/ha | % Efficacy |
|---|---|---|
| (I-10) | 100 | 88 |
| (I-11) | 100 | 93 |
| (I-20) | 100 | 100 |
| (I-22) | 100 | 100 |

TABLE A-continued

Podosphaera test (apple) / protective

| Active compound | | Application rate of active compound in g/ha | % Efficacy |
|---|---|---|---|
| (I-23) | *[structure: 4-trifluoromethyl-2-methyl-thiazole-5-carboxamide linked to biphenyl with CH=N-O-CH₂CH₃ group]* | 100 | 100 |
| (I-24) | *[structure: 3-trifluoromethyl-1-methyl-pyrazole-4-carboxamide linked to biphenyl with C(CH₃)=N-O-CH₂CH₃ group]* | 100 | 75 |
| (I-26) | *[structure: 3-trifluoromethyl-1-methyl-pyrazole-4-carboxamide linked to biphenyl with CH=N-O-CH(CH₃)₂ group]* | 100 | 100 |
| (I-28) | *[structure: 3-trifluoromethyl-1-methyl-pyrazole-4-carboxamide linked to biphenyl with CH=N-O-CH₂CH₂CH₃ group]* | 100 | 99 |

TABLE A-continued

Podosphaera test (apple) / protective

| Active compound | Application rate of active compound in g/ha | % Efficacy |
|---|---|---|
| (I-41) | 100 | 98 |
| (I-47) | 100 | 100 |
| (I-49) | 100 | 100 |

TABLE A-continued

Podosphaera test (apple) / protective

| Active compound | Application rate of active compound in g/ha | % Efficacy |
|---|---|---|
| (I-50) | 100 | 93 |
| (I-51) | 100 | 100 |
| (I-52) | 100 | 77 |

Example B

Sphacrotheca Test (cucumber)/Protective

| Solvent: | 24.5 parts by weight of acetone |
| | 24.5 parts by weight of dimethylacetamide |
| Emulsifier: | 1.0 part by weight of alkyl-aryl polyglycol ether |

To produce a suitable preparation of active compound, 1 part by weight of active compound is mixed with the stated amounts of solvent and emulsifier, and the concentrate is diluted with water to the desired concentration.

To test for protectivity activity, young plants are sprayed with the preparation of active compound at the stated application rate. After the spray coating has dried on, the plants are inoculated with an aqueous spore suspension of *Sphaerotheca fuliginea*. The plants are then placed in a greenhouse at approximately 23° C. and a relative atmospheric humidity of approximately 70%.

Evaluation is carried out 10 days after the inoculation. 0% means an efficacy which corresponds to that of the control, whereas an efficacy of 100% means that no infection is observed.

In this test, for example, the following compounds according to the invention of the Preparation Examples exhibit an activity which is superior to that of the prior art:

TABLE B

Sphaerotheca test (cucumber) / protective

| Active compound | | Application rate of active compound in g/ha | % Efficacy |
|---|---|---|---|
| (I-1) | [structure: 2-methyl-4-(trifluoromethyl)thiazole-5-carboxamide linked to biphenyl with =N-OCH₃ oxime] | 100 | 100 |
| (I-3) | [structure: 2-methyl-4-(trifluoromethyl)thiazole-5-carboxamide linked to biphenyl with =N-O-butyl oxime] | 100 | 100 |
| (I-4) | [structure: 2-methyl-4-(trifluoromethyl)thiazole-5-carboxamide linked to biphenyl with =N-OCH₂CH₃ oxime] | 100 | 93 |
| (I-5) | [structure: 2-methyl-4-(trifluoromethyl)thiazole-5-carboxamide linked to biphenyl with =N-O-isopropyl oxime] | 100 | 100 |

TABLE B-continued

Sphaerotheca test (cucumber) / protective

| Active compound | Application rate of active compound in g/ha | % Efficacy |
|---|---|---|
| (I-10) | 100 | 88 |
| (I-11) | 100 | 95 |
| (I-20) | 100 | 100 |
| (I-22) | 100 | 100 |

TABLE B-continued

Sphaerotheca test (cucumber) / protective

| Active compound | Application rate of active compound in g/ha | % Efficacy |
|---|---|---|
| (I-23) | 100 | 100 |
| (I-24) | 100 | 92 |
| (I-26) | 100 | 100 |
| (I-28) | 100 | 100 |

TABLE B-continued

Sphaerotheca test (cucumber) / protective

| Active compound | | Application rate of active compound in g/ha | % Efficacy |
|---|---|---|---|
| (I-41) | | 100 | 72 |
| (I-47) | | 100 | 100 |
| (I-49) | | 100 | 100 |

TABLE B-continued

Sphaerotheca test (cucumber) / protective

| Active compound | Application rate of active compound in g/ha | % Efficacy |
|---|---|---|
| (I-50) | 100 | 97 |
| (I-51) | 100 | 100 |
| (I-52) | 100 | 97 |

Example C

Venturia Test (apple)/Protective

| Solvent: | 24.5 parts by weight of acetone |
| | 24.5 parts by weight of dimethylacetamide |
| Emulsifier: | 1.0 part by weight of alkyl-aryl polyglycol ether |

To produce a suitable preparation of active compound, 1 part by weight of active compound is mixed with the stated amounts of solvent and emulsifier, and the concentrate is diluted with water to the desired concentration.

To test for protectivity activity, young plants are sprayed with the preparation of active compound at the stated application rate. After the spray coating has dried on, the plants are inoculated with an aqueous conidia suspension of the apple scab pathogen Venturia inaequalis and then remain in an incubation cabin at approximately 20° C. and 100% relative atmospheric humidity for 1 day.

The plants are then placed in a greenhouse at approximately 21° C. and a relative atmospheric humidity of approximately 90%.

Evaluation is carried out 12 days after the inoculation. 0% means an efficacy which corresponds to that of the control, whereas an efficacy of 100% means that no infection is observed.

In this test, for example, the following compounds according to the invention of the Preparation Examples exhibit an activity which is superior to that of the prior art:

TABLE C

Venturia test (apple) / protective

| Active compound | | Application rate of active compound in g/ha | % Efficacy |
|---|---|---|---|
| (I-1) | (structure) | 100 | 100 |
| (I-3) | (structure) | 100 | 100 |
| (I-4) | (structure) | 100 | 100 |
| (I-5) | (structure) | 100 | 100 |

TABLE C-continued

Venturia test (apple) / protective

| Active compound | | Application rate of active compound in g/ha | % Efficacy |
|---|---|---|---|
| (I-10) | [structure: 1-methyl-3-(trifluoromethyl)-pyrazole-4-carboxamide linked to biphenyl with CH=N-OCH₃] | 100 | 88 |
| (I-11) | [structure: 3-(difluoromethyl)-1-methyl-pyrazole-4-carboxamide linked to biphenyl with CH=N-OCH₃] | 100 | 100 |
| (I-20) | [structure: 2-chloronicotinamide linked to biphenyl with CH=N-OCH₃] | 100 | 100 |
| (I-22) | [structure: 1-methyl-3-(trifluoromethyl)-pyrazole-4-carboxamide linked to biphenyl with CH=N-O-propyl] | 100 | 100 |

TABLE C-continued

Venturia test (apple) / protective

| Active compound | | Application rate of active compound in g/ha | % Efficacy |
|---|---|---|---|
| (I-23) | | 100 | 100 |
| (I-24) | | 100 | 100 |
| (I-26) | | 100 | 100 |
| (I-28) | | 100 | 100 |

TABLE C-continued
Venturia test (apple) / protective
| Active compound | Application rate of active compound in g/ha | % Efficacy |
|---|---|---|
| (I-41) 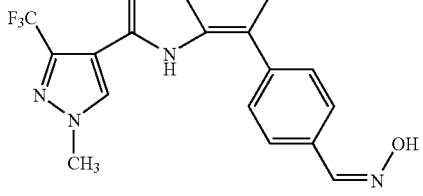 | 100 | 100 |
| (I-47) 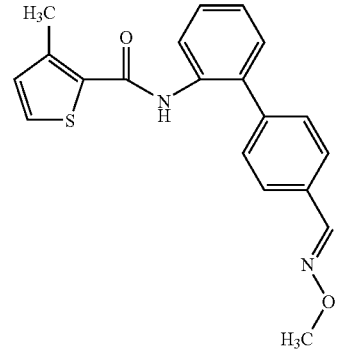 | 100 | 100 |
| (I-49) 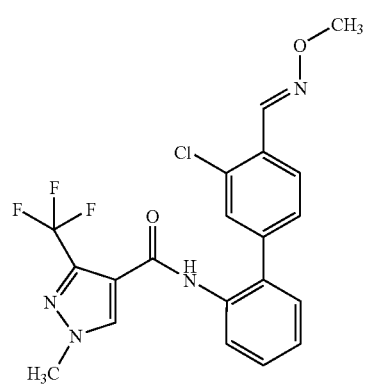 | 100 | 100 |

TABLE C-continued

Venturia test (apple) / protective

| Active compound | Application rate of active compound in g/ha | % Efficacy |
|---|---|---|
| (I-50) [structure] | 100 | 100 |
| (I-51) [structure] | 100 | 100 |
| (I-52) [structure] | 100 | 100 |

Example D

Puccinia Test (wheat)/Protective

| | |
|---|---|
| Solvent: | 25 parts by weight of N,N-dimethylacetamide |
| Emulsifier: | 0.6 part by weight of alkylaryl polyglycol ether |

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound at the stated application rate. After the spray coating has dried on, the plants are sprayed with a conidia suspension of *Puccinia recondite*. The plants remain in an incubation cabin at 20° C. and 100% relative atmospheric humidity for 48 hours.

The plants are then placed in a greenhouse at a temperature of approximately 20° C. and a relative atmospheric humidity of 80% to promote the development of rust pustules.

Evaluation is carried out 10 days after the inoculation. 0% means an efficacy which corresponds to that of the control, whereas an efficacy of 100% means that no infection is observed.

In this test, for example, the following compounds according to the invention of the Preparation Examples exhibit an activity which is superior to that of the prior art:

TABLE D

Puccinia test (wheat) / protective

| Active compound | | Application rate of active compound in g/ha | % Efficacy |
|---|---|---|---|
| (I-1) | 4-(trifluoromethyl)-2-methyl-thiazole-5-carboxylic acid [2'-((methoxyimino)methyl)biphenyl-2-yl]amide | 250 | 100 |
| (I-3) | 4-(trifluoromethyl)-2-methyl-thiazole-5-carboxylic acid [2'-((butoxyimino)methyl)biphenyl-2-yl]amide | 250 | 100 |
| (I-10) | 3-(trifluoromethyl)-1-methyl-pyrazole-4-carboxylic acid [2'-((methoxyimino)methyl)biphenyl-2-yl]amide | 250 | 100 |

TABLE D-continued

Puccinia test (wheat) / protective

| Active compound | Application rate of active compound in g/ha | % Efficacy |
|---|---|---|
| (I-20) 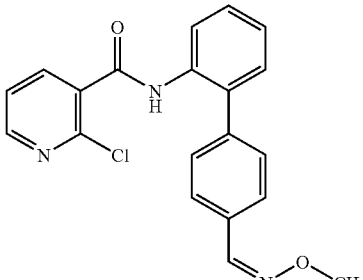 | 250 | 100 |
| (I-49) 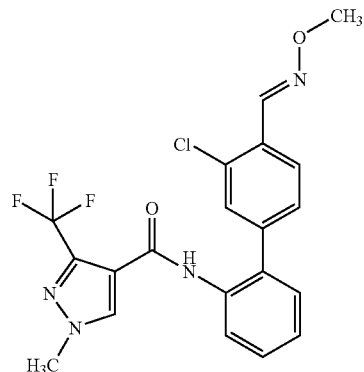 | 250 | 100 |
| (I-51) 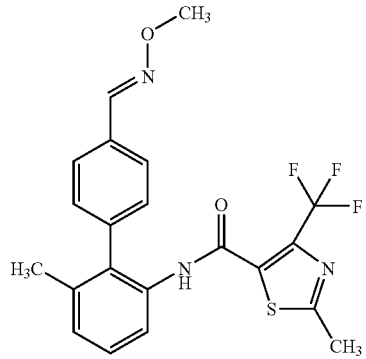 | 250 | 100 |

Example E

Alternaria Test (tomato)/Protective

| Solvent: | 49 parts by weight of N,N-dimethylformamide |
| Emulsifier: | 1 part by weight of alkylaryl polyglycol ether |

To produce a suitable preparation of active compound, 1 part by weight of active compound is mixed with the stated amounts of solvent and emulsifier, and the concentrate is diluted with water to the desired concentration.

To test for protective activity, young tomato plants are sprayed with the preparation of active compound at the stated application rate. 1 day after the treatment, the plants are inoculated with a spore suspension of *Alternaria* solani and then remain at 100% rel. humidity and 20° C. for 24 h. The plants then remain at 96% rel. atmospheric humidity and a temperature of 20° C.

Evaluation is carried out 7 days after the inoculation. 0% means an efficacy which corresponds to that of the control, whereas an efficacy of 100% means that no infection is observed.

In this test, for example, the following compounds according to the invention of the Preparation Examples exhibit an activity which is superior to that of the prior art:

TABLE E

Alternaria test (tomato) / protective

| Active compound | Application rate of active compound in g/ha | % Efficacy |
|---|---|---|
| (I-1) | 750 | 100 |
| (I-2) | 750 | 100 |
| (I-6) | 750 | 90 |
| (I-11) | 750 | 95 |

Example F

Inhibition Test on Giant Colonies of Basidiomycetes

Mycelium sections were removed from colonies of *Gloeophyllum trabeum, Coniophora puteana, Poria placenta, Lentinus tigrinus* and *Coriolus versicolor* and incubated on an agar medium containing malt extract peptone at 26° C. The inhibition of hyphal growth on active-compound-containing media was compared with the longitudinal growth on media without an addition of active compound and rated as per cent inhibition.

In this test, for example, the following compounds according to the invention of the Preparation Examples exhibit good activity:

TABLE F

Inhibition test on giant colonies of Basidiomycetes

| Active compound | | Application rate of active compound in ppm | % efficacy |
|---|---|---|---|
| (I-1) | 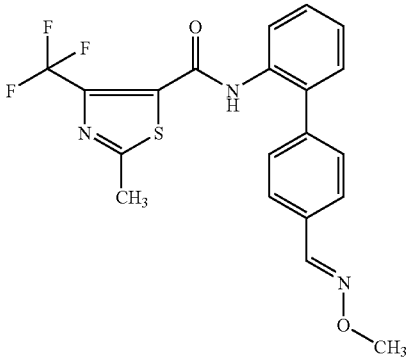 | 6 | 100 |
| (I-10) | 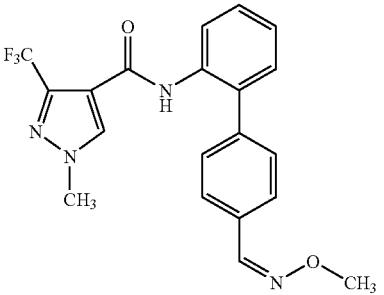 | 6 | 100 |
| (I-11) | 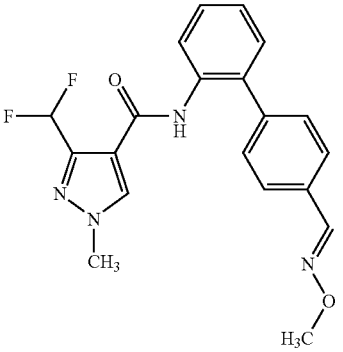 | 6 | 100 |

TABLE F-continued

Inhibition test on giant colonies of Basidiomycetes

| Active compound | Application rate of active compound in ppm | % efficacy |
|---|---|---|
| (I-12) 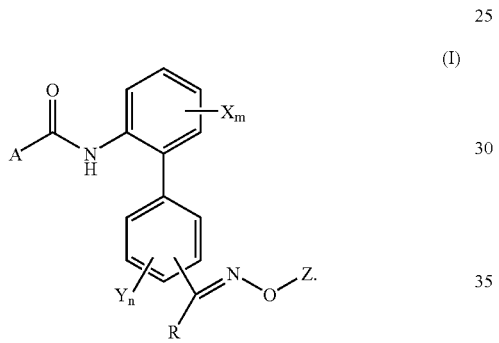 | 6 | 100 |

What is claimed is:

1. A biphenylcarboxamide of the formula (I)

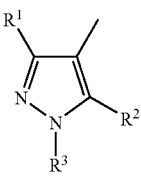

in which

R represents hydrogen, $C_1$–$C_6$-alkyl, $C_3$–$C_6$-cycloalkyl, or $C_1$–$C_6$-halogenoalkyl having 1 to 5 halogen atoms, Z represents hydrogen, $C_1$–$C_6$-alkyl, or $C_1$–$C_6$-halogenoalkyl having 1 to 5 halogen atoms, X and Y independently of one another each represent halogen, nitro, cyano, hydroxy, carboxyl, $C_1$–$C_8$-alkyl, $C_1$–$C_6$-halogenoalkyl having 1 to 5 halogen atoms, $C_1$–$C_8$-alkoxy, $C_1$–$C_6$-halogenoalkoxy having 1 to 5 halogen atoms, $C_1$–$C_8$-alkylthio, $C_1$–$C_6$-halogenoalkylthio having 1 to 5 halogen atoms, $C_2$–$C_8$-alkenyloxy, $C_2$–$C_8$-halogenoalkenyloxy having 1 to 5 halogen atoms, $C_3$–$C_8$-alkynyloxy, $C_3$–$C_8$-halogenoalkynyloxy having 1 to 5 halogen atoms, $C_3$–$C_8$-cycloalkyl, $C_1$–$C_8$-alkoxycarbonyl, $C_1$–$C_8$-alkylsulphinyl, $C_1$–$C_8$-alkylsulphonyl, $C_1$–$C_8$halogenoalkylsulphinyl having 1 to 5 halogen atoms, $C_1$–$C_8$-halogeno-alkylsulphonyl having 1 to 5 halogen atoms, or $C_1$–$C_6$-alkoximino-$C_1$–$C_6$-alkyl, m represents integers from 0 to 3, with the proviso that X represents identical or different radicals if m represents 2 or 3, n represents integers from 0 to 4, with the proviso that Y represents identical or different radicals, if n represents 2, 3, or 4, and A represents a radical of the formula $$R^1 \quad \begin{array}{c} \\ \diagdown \\ N \\ | \\ R^3 \end{array} \quad R^2$$

in which (α) $R^1$ represents hydrogen, cyano, halogen, nitro, $C_1$–$C_4$-alkyl, $C_1$–$C_4$-halogenoalkyl having 1 to 5 halogen atoms, $C_3$–$C_6$-cycloalkyl, $C_1$–$C_4$-alkoxy, $C_1$–$C_4$-halogenoalkoxy having 1 to 5 halogen atoms, $C_1$–$C_4$-alkylthio, $C_1$–$C_4$-halogenoalkylthio having 1 to 5 halogen atoms, aminocarbonyl, or aminocarbonyl-$C_1$–$C_4$-alkyl, $R^2$ represents hydrogen, cyano, $C_1$–$C_4$-alkyl, $C_1$–$C_4$-alkoxy, or $C_1$–$C_4$-alkylthio, and $R^3$ represents hydrogen, $C_1$–$C_4$-alkyl, $C_1$–$C_4$-halogenoalkyl having 1 to 5 halogen atoms, hydroxy-$C_1$–$C_4$-alkyl, $C_2$–$C_6$-alkenyl, $C_3$–$C_6$-cycloalkyl, $C_1$–$C_4$-alkylthio-$C_1$–$C_4$-alkyl, $C_1$–$C_4$-halogenoalkylthio-$C_1$–$C_4$-alkyl having 1 to 5 halogen atoms, $C_1$–$C_4$-alkoxy-$C_1$–$C_4$-alkyl, $C_1$–$C_4$-halogenoalkoxy-$C_1$–$C_4$-alkyl having 1 to 5 halogen atoms, or phenyl, or (β) $R^1$ represents hydrogen, cyano, halogen, nitro, $C_1$–$C_4$-halogenoalkyl having 1 to 5 halogen atoms, $C_3$–$C_6$-cycloalkyl, $C_1$–$C_4$-alkoxy, $C_1$–$C_4$-halogenoalkoxy having 1 to 5 halogen atoms, $C_1$–$C_4$-alkylthio, $C_1$–$C_4$-halogenoalkylthio having 1 to 5 halogen atoms, aminocarbonyl, or aminocarbonyl-$C_1$–$C_4$-alkyl, $R^2$ represents fluorine, and $R^3$ represents hydrogen, $C_1$–$C_4$-alkyl, $C_1$–$C_4$-halogenoalkyl having 1 to 5 halogen atoms, hydroxy-$C_1$–$C_4$-alkyl, $C_2$–$C_6$-alkenyl, $C_3$–$C_6$-cycloalkyl, $C_1$–$C_4$-alkylthio-$C_1$–$C_4$-alkyl, $C_1$–$C_4$-halogenoalkylthio-$C_1$–$C_4$-alkyl having 1 to 5 halogen atoms, $C_1$–$C_4$-alkoxy-$C_1$–$C_4$-alkyl, $C_1$–$C_4$-halogenoalkoxy-$C_1$–$C_4$-alkyl having 1 to 5 halogen atoms, or phenyl, or (γ) $R^1$ represents hydrogen, cyano, halogen, nitro, $C_1$–$C_4$-alkyl, $C_1$–$C_4$-halogenoalkyl having 1 to 5 halogen atoms, $C_3$–$C_6$-cycloalkyl, $C_1$–$C_4$-alkoxy, $C_1$–$C_4$-halogenoalkoxy having 1 to 5 halogen atoms, $C_1$–$C_4$-alkylthio, $C_1$–$C_4$-halogenoalkylthio having 1 to 5 halogen atoms, aminocarbonyl, or aminocarbonyl-$C_1$–$C_4$-alkyl, $R^2$ represents fluorine, and $R^3$ represents hydrogen, $C_1$–$C_4$-halogenoalkyl having 1 to 5 halogen atoms, hydroxy-$C_1$–$C_4$-alkyl, $C_2$–$C_6$-alkenyl, $C_3$–$C_6$-cycloalkyl, $C_1$–$C_4$-alkylthio-$C_1$–$C_4$-alkyl, $C_1$–$C_4$-halogenoalkylthio-$C_1$–$C_4$-alkyl having 1 to 5 halogen atoms, $C_1$–$C_4$alkoxy-$C_1$–$C_4$-alkyl, $C_1$–$C_4$-halogenoalkoxy-$C_1$–$C_4$-alkyl having 1 to 5 halogen atoms or phenyl.

2. A biphenylcarboxamide of the formula (I) according to claim 1 in which

R represents hydrogen, $C_1$–$C_4$-alkyl, or $C_3$–$C_6$-Cycloalkyl, or $C_1$–$C_4$-halogenoalkyl having 1 to 5 halogen atoms, Z represents hydrogen, $C_1$–$C_4$-alkyl, or $C_1$–$C_4$-halogenoalkyl having 1 to 5 halogen atoms, X and Y independently of one another each represent fluorine, chlorine, bromine, nitro, cyano, hydroxy, carboxyl, $C_1$–$C_6$-alkyl, $C_1$–$C_2$-halogenoalkyl having 1 to 5 fluorine, chlorine, and/or bromine atoms, $C_1$–$C_6$-alkoxy, $C_1$–$C_2$-halogenoalkoxy having 1 to 5 fluorine, chlorine and/or bromine atoms, $C_1$–$C_6$-alkylthio, $C_1$–$C_2$-halogenoalkylthio having 1 to 5 fluorine, chlorine, and/or bromine atoms, $C_2$–$C_6$-alkenyloxy, $C_2$–$C_6$-halogenoalkenyloxy having 1 to 5 halogen atoms, $C_3$–$C_6$-alkynyloxy, $C_3$–$C_6$-halogenoalkynyloxy having 1 to 5 halogen atoms, $C_3$–$C_7$-cycloalkyl, $C_1$–$C_4$-alkoxycarbonyl, $C_1$–$C_6$-alkylsulphinyl, $C_1$–$C_6$-alkylsulphonyl, $C_1$–$C_6$-halogenoalkylsulphinyl having 1 to 5 halogen atoms, $C_1$–$C_6$-halogenoalkylsulphonyl having 1 to 5 halogen atoms, or $C_1$–$C_4$-alkoximino-$C_1$–$C_4$-alkyl, m represents integers from 0 to 3, with the proviso that X represents identical or different radicals if m represents 2 or 3, n represents integers from 0 to 4, with the proviso that Y represents identical or different radicals if n represents 2, 3, or 4, and A represents a radical of the formula

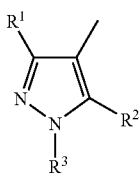

in which (α) $R^1$ represents hydrogen, cyano, fluorine, chlorine, bromine, iodine, methyl, ethyl, isopropyl, $C_1$–$C_2$-halogenoalkyl having 1 to 5 fluorine, chlorine, and/or bromine atoms, cyclopropyl, methoxy, ethoxy, $C_1$–$C_2$-halogenoalkoxy having 1 to 5 fluorine, chlorine, and/or bromine atoms, methylthio, ethylthio, trifluoromethylthio, difluoromethylthio, aminocarbonyl, aminocarbonylmethyl, or aminocarbonylethyl, $R^2$ represents hydrogen, methyl, ethyl, methoxy, ethoxy, methylthio, or ethylthio, and $R^3$ represents hydrogen, methyl, ethyl, n-propyl, isopropyl, $C_1$–$C_2$-halogenoalkyl having 1 to 5 fluorine, chlorine, and/or bromine atoms, hydroxymethyl, hydroxyethyl, cyclopropyl, cyclopentyl, cyclohexyl, or phenyl, or (β) $R^1$ represents hydrogen, cyano, fluorine, chlorine, bromine, iodine, $C_1$–$C_2$-halogenoalkyl having 1 to 5 fluorine, chlorine, and/or bromine atoms, cyclopropyl, methoxy, ethoxy, $C_1$–$C_2$-halogenoalkoxy having 1 to 5 fluorine, chlorine, and/or bromine atoms, methylthio, ethylthio, trifluoromethylthio, difluoromethylthio, amino-carbonyl, aminocarbonylmethyl, or aminocarbonylethyl, $R^2$ represents fluorine, and $R^3$ represents hydrogen, methyl, ethyl, n-propyl, isopropyl, $C_1$–$C_2$-halogenoalkyl having 1 to 5 fluorine, chlorine, and/or bromine atoms, hydroxymethyl, hydroxyethyl, cyclopropyl, cyclopentyl, cyclohexyl, or phenyl, or (γ) $R^1$ represents hydrogen, cyano, fluorine, chlorine, bromine, iodine, methyl, ethyl, isopropyl, $C_1$–$C_2$-halogenoalkyl having 1 to 5 fluorine, chlorine, and/or bromine atoms, cyclopropyl, methoxy, ethoxy, $C_1$–$C_2$-halogenoalkoxy having 1 to 5 fluorine, chlorine, and/or bromine atoms, methylthio, ethylthio, trifluoromethylthio, difluoromethylthio, aminocarbonyl, aminocarbonylmethyl, or aminocarbonylethyl, $R^2$ represents fluorine, and $R^3$ represents hydrogen, $C_1$–$C_2$-halogenoalkyl having 1 to 5 fluorine, chlorine, and/or bromine atoms, hydroxymethyl, hydroxyethyl, cyclopropyl, cyclopentyl, cyclohexyl, or phenyl.

3. A biphenylcarboxamide of the formula (I) according to claim 1 in which

R represents hydrogen or $C_1$–$C_4$-alkyl,

Z represents hydrogen or $C_1$–$C_4$-alkyl,

X and Y independently of one another each represent fluorine, chlorine, bromine, nitro, cyano, hydroxy, carboxyl, methyl, ethyl, n-propyl, isopropyl, n-butyl, sec-butyl, i-butyl, tert-butyl, trichloromethyl, trifluoromethyl, difluoromethyl, difluorochloromethyl, methoxy, ethoxy, difluoromethoxy, trifluoromethoxy, methylthio, trifluoromethylthio, difluorochloromethylthio, allyloxy, propargyloxy, cyclopropyl, cyclopentyl, cyclohexyl, cycloheptyl, methoxycarbonyl, ethoxycarbonyl, methoximinomethyl, ethoximinomethyl, methoximinoethyl, or ethoximinoethyl, m represents integers from 0 to 3, with the proviso that X represents identical or different radicals if m represents 2 or 3, n represents the numbers 0 to 4, with the proviso that Y represents identical or different radicals if n represents 2, 3, or 4, and A represents a radical of the formula

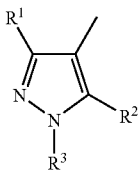

in which (α) $R^1$ represents hydrogen, fluorine, chlorine, bromine, iodine, methyl, ethyl, isopropyl, monofluoromethyl, difluoromethyl, trifluoromethyl, difluorochloromethyl, trichloromethyl, cyclopropyl, methoxy, ethoxy, trifluoromethoxy, trichloromethoxy, methylthio, ethylthio, trifluoromethylthio, or difluoromethylthio, $R^2$ represents hydrogen, methyl, ethyl, methoxy, ethoxy, methylthio, or ethylthio, and $R^3$ represents hydrogen, methyl, ethyl, trifluoromethyl, difluoromethyl, hydroxymethyl, hydroxyethyl, or phenyl, or (β) $R^1$ represents hydrogen, fluorine, chlorine, bromine, iodine, monofluoromethyl, difluoromethyl, trifluoromethyl, difluorochloromethyl, trichloromethyl, cyclopropyl, methoxy, ethoxy, trifluoromethoxy, trichloromethoxy, methylthio, ethylthio, trifluoromethylthio, or difluoromethylthio, and $R^2$ represents fluorine, and $R^3$ represents hydrogen, methyl, ethyl, trifluoromethyl, difluoromethyl, hydroxymethyl, hydroxyethyl, or phenyl, or (γ) $R^1$ represents hydrogen, fluorine, chlorine, bromine, iodine, methyl, ethyl, isopropyl, monofluoromethyl, difluoromethyl, trifluoromethyl, difluorochloromethyl, trichloromethyl, cyclopropyl, methoxy, ethoxy, trifluoromethoxy, trichloromethoxy, methylthio, ethylthio, trifluoromethylthio, or difluoromethylthio, $R^2$ represents fluorine, and $R^3$ represents hydrogen, trifluoromethyl, difluoromethyl, hydroxymethyl, hydroxyethyl, or phenyl.

4. A process for preparing a biphenylcarboxamide of the formula (I) according to claim 1 comprising (a) reading a carboxylic acid derivative of the formula (II)

(II)

in which

A is as defined for formula (I) in claim 1, and

G represents halogen, hydroxy, or $C_1$–$C_6$-alkoxy, with an aniline derivative of the formula (III)

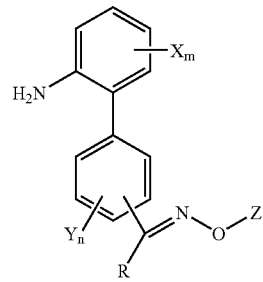

(III)

in which R, Z, X, Y, m, and n are each as defined for formula (I) in claim 1, optionally in the presence of a catalyst, optionally in the presence of an acid binder, and optionally in the presence of a diluent, or (b) reacting a carboxamide derivative of the formula (IV)

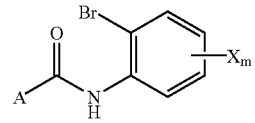

(IV)

in which A, X, and m are each as defined for formula (I) in claim 1, with a boronic acid derivative of the formula (V)

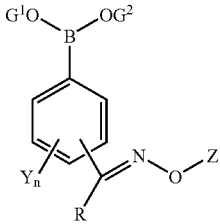

(V)

in which

R, Z, Y, and n are each as defined for formula (I) in claim 1, and $G^1$ and $G^2$ each represent hydrogen or together represent tetramethylethylene, optionally in the presence of an acid binder and optionally in the presence of a diluent, or (c) reacting a carboxamide-boronic acid derivative of the formula (VI)

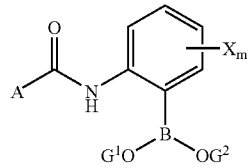

(VI)

in which

A, X, and m are each as defined for formula (I) in claim 1, and

G¹ and G² each represent hydrogen or together represent tetramethylethylene, with a phenyloxime derivative of the formula (VII)

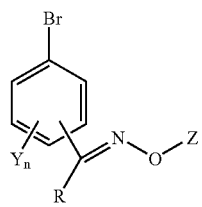
(VII)

in which R, Z, Y, and n are each as defined for formula (I) in claim 1, optionally in the presence of an acid binder and optionally in the presence of a diluent, or (d) reacting biphenylacyl derivative of the formula (VIII)

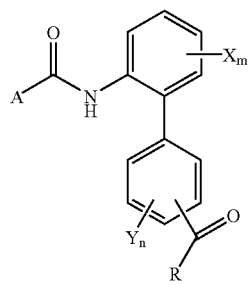
(VIII)

in which A, R, X, Y, m, and n are each as defined for formula (I) in claim 1, with an alkoxamine of the formula (IX)

Z-O—NH₂ x HCl (IX)

in which each Z is as defined for formula (I) in claim 1, optionally in the presence of an acid binder and optionally in the presence of a diluent, or (e) reading a hydroxyamine derivative of the formula (I-a)

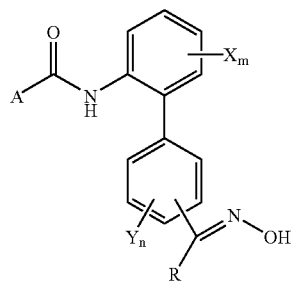
(I-a)

in which A, R, X, Y, m, and n are each as defined for formula (I) in claim 1, with a compound of the formula (x)

Z¹-E (x)

in which

Z¹ represents $C_1$–$C_6$-alkyl, and

E represents chlorine, bromine, iodine, methanesulphonyl, or p-toluenesulphonyl, or Z¹ and E together represent (di-$C_1$–$C_6$-alkyl) sulphate, optionally in the presence of an acid binder and optionally in the presence of a diluent, or (f) reacting a carboxamide derivative of the formula (IV)

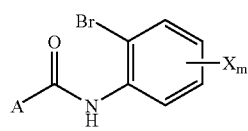
(IV)

in which A, X, and m are each as defined for formula (I) in claim 1, with a phenyloxime derivative of the formula (VII)

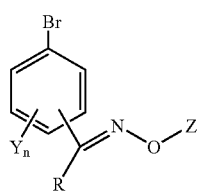
(VII)

in which R, Z, Y, and n are each as defined for formula (I) in claim 1, in the presence of a palladium or platinum catalyst and in the presence of 4,4,4',4',5,5,5',5'-octamethyl-2,2'-bis-1,3,2-dioxaborolane, and optionally in the presence of an acid binder and optionally in the presence of a diluent.

5. A composition for controlling undesirable microorganisms comprising an effective amount of one or more biphenylcarboxamides of the formula (I) according to claim 1 and extenders and/or surfactants.

6. A method for controlling undesirable microorganisms comprising applying a biphenylcarboxamide of the formula (I) according to claim 1 to the microorganisms and/or their habitat.

* * * * *